(12) United States Patent
Kesil et al.

(10) Patent No.: US 8,547,110 B2
(45) Date of Patent: Oct. 1, 2013

(54) IMPEDANCE SENSING SYSTEMS AND METHODS FOR USE IN MEASURING CONSTITUENTS IN SOLID AND FLUID OBJECTS

(75) Inventors: Boris Kesil, San Jose, CA (US); Yury Nikolenko, San Jose, CA (US)

(73) Assignee: Adem, LLC, Santa Clara, CA (US)

( * ) Notice: Subject to any disclaimer, the term of this patent is extended or adjusted under 35 U.S.C. 154(b) by 413 days.

(21) Appl. No.: 12/887,887

(22) Filed: Sep. 22, 2010

(65) Prior Publication Data
US 2011/0068807 A1 Mar. 24, 2011

Related U.S. Application Data

(60) Provisional application No. 61/244,584, filed on Sep. 22, 2009.

(51) Int. Cl.
*G01R 27/04* (2006.01)
(52) U.S. Cl.
USPC .............................. 324/633; 324/652; 324/668
(58) Field of Classification Search
USPC .................. 324/633, 652, 655, 668, 675, 682, 324/654, 445, 708, 76.51, 76.76
See application file for complete search history.

(56) References Cited

U.S. PATENT DOCUMENTS

| | | | |
|---|---|---|---|
| 2,583,724 A | | 1/1952 | Broding |
| 3,774,103 A | * | 11/1973 | Laukien ........................ 324/313 |
| 4,058,766 A | | 11/1977 | Vogel et al. |
| 4,334,604 A | * | 6/1982 | Davies .......................... 194/319 |
| 4,433,286 A | | 2/1984 | Capots |
| 5,003,262 A | | 3/1991 | Egner et al. |
| 5,091,704 A | | 2/1992 | Kopera |
| 5,132,617 A | | 7/1992 | Leach et al. |
| 5,213,655 A | | 5/1993 | Leach et al. |
| 5,242,524 A | | 9/1993 | Leach et al. |
| 5,343,146 A | | 8/1994 | Koch et al. |
| 5,516,399 A | | 5/1996 | Balconi-Lamica et al. |
| 5,541,510 A | | 7/1996 | Danielson |
| 5,550,478 A | | 8/1996 | Kopera |
| 5,559,428 A | | 9/1996 | Li et al. |

(Continued)

FOREIGN PATENT DOCUMENTS

| | | | |
|---|---|---|---|
| GB | 1471480 A | | 4/1977 |
| SU | 1408391 A | * | 7/1988 |

(Continued)

OTHER PUBLICATIONS

International Search Report and Written Opinion for PCT/US2010/0219824, dated Feb. 10, 2011.

(Continued)

*Primary Examiner* — Vincent Q Nguyen
(74) *Attorney, Agent, or Firm* — Pergament Gilman & Cepeda LLP

(57) ABSTRACT

Devices and methods of the invention can be used in many industries, including, but not limited to, utilities, agriculture, food, textile, pharmaceutical, photovoltaic and semiconductor, medical devices, chemical and petro-chemical, material science, and defense, where monitoring and/or analysis of various properties of materials are desired. Sensors and methods of using same are provided for measuring at least one impedance of an object under test (or a tested object) at a predetermined frequency and/or a predetermined frequency range, particularly where resonance conditions are provided for such measurement.

45 Claims, 24 Drawing Sheets

(56) References Cited

U.S. PATENT DOCUMENTS

| | | |
|---|---|---|
| 5,644,221 A | 7/1997 | Li et al. |
| 5,659,492 A | 8/1997 | Li et al. |
| 5,660,672 A | 8/1997 | Li et al. |
| 5,663,637 A | 9/1997 | Li et al. |
| 5,731,697 A | 3/1998 | Li et al. |
| 5,770,948 A | 6/1998 | Li et al. |
| 5,889,401 A | 3/1999 | Jourdain et al. |
| 5,942,893 A | 8/1999 | Terpay |
| 6,072,313 A | 6/2000 | Li et al. |
| 6,310,480 B1 | 10/2001 | Cohen et al. |
| 6,377,039 B1 | 4/2002 | Goldfine et al. |
| 6,380,747 B1 | 4/2002 | Goldfine et al. |
| 6,404,197 B1 | 6/2002 | Anderson et al. |
| 6,404,199 B1 * | 6/2002 | Fujita et al. .......... 324/318 |
| 6,407,546 B1 | 6/2002 | Le et al. |
| 6,433,541 B1 | 8/2002 | Lehman et al. |
| 6,448,795 B1 | 9/2002 | Ermakov et al. |
| 6,511,851 B1 | 1/2003 | Payne et al. |
| 6,558,229 B2 | 5/2003 | Kimura et al. |
| 6,563,308 B2 | 5/2003 | Nagano et al. |
| 6,593,738 B2 | 7/2003 | Kesil et al. |
| 6,602,724 B2 | 8/2003 | Redeker et al. |
| 6,621,264 B1 | 9/2003 | Lehman et al. |
| 6,657,433 B1 | 12/2003 | Locatelli et al. |
| 6,663,469 B2 | 12/2003 | Kimura et al. |
| 6,669,557 B2 | 12/2003 | Adams et al. |
| 6,707,540 B1 | 3/2004 | Lehman et al. |
| 6,741,076 B2 | 5/2004 | Le |
| 6,762,604 B2 | 7/2004 | Le |
| 6,815,947 B2 | 11/2004 | Scheiner et al. |
| 6,878,038 B2 | 4/2005 | Johansson et al. |
| 6,891,380 B2 | 5/2005 | Kesil et al. |
| 6,920,399 B2 | 7/2005 | Priev et al. |
| 6,923,711 B2 | 8/2005 | Laursen et al. |
| 6,966,816 B2 | 11/2005 | Swedek et al. |
| 6,975,107 B2 | 12/2005 | Hanawa et al. |
| 6,977,503 B2 | 12/2005 | Prado |
| 7,008,296 B2 | 3/2006 | Swedek et al. |
| 7,008,297 B2 | 3/2006 | Johansson et al. |
| 7,016,795 B2 | 3/2006 | Swedek et al. |
| 7,043,402 B2 | 5/2006 | Phillips et al. |
| 7,046,001 B2 | 5/2006 | Tada et al. |
| 7,070,476 B2 | 7/2006 | Lehman et al. |
| 7,074,109 B1 | 7/2006 | Bennett et al. |
| 7,078,894 B2 | 7/2006 | Tada et al. |
| 7,095,230 B2 | 8/2006 | Blumich et al. |
| 7,135,870 B2 | 11/2006 | Mohajer et al. |
| 7,195,536 B2 | 3/2007 | Swedek et al. |
| 7,198,545 B1 | 4/2007 | Korovin et al. |
| 7,219,024 B2 | 5/2007 | Gamache et al. |
| 7,247,080 B1 | 7/2007 | Bennett et al. |
| 7,332,902 B1 | 2/2008 | Vermeire et al. |
| 7,352,186 B2 | 4/2008 | Hasegawa et al. |
| 7,374,477 B2 | 5/2008 | Birang et al. |
| 7,500,901 B2 | 3/2009 | Swedek et al. |
| 7,508,201 B2 | 3/2009 | Tada et al. |
| 7,514,938 B2 | 4/2009 | Publicover et al. |
| 7,591,708 B2 | 9/2009 | Birang et al. |
| 7,619,414 B2 | 11/2009 | Yamamoto et al. |
| 7,635,331 B2 | 12/2009 | Kim et al. |
| 7,659,731 B2 | 2/2010 | Lin et al. |
| 7,682,221 B2 | 3/2010 | Swedek et al. |
| 7,714,572 B2 | 5/2010 | Tada et al. |
| 7,737,038 B2 | 6/2010 | Lee et al. |
| 7,795,866 B2 | 9/2010 | Fujita |
| 7,822,500 B2 | 10/2010 | Kobayashi et al. |
| 7,836,756 B2 | 11/2010 | Boudaoud et al. |
| 7,912,661 B2 | 3/2011 | Zeng et al. |
| 8,106,657 B2 | 1/2012 | Sakellariou et al. |
| 2003/0181827 A1 * | 9/2003 | Hojeibane et al. ........... 600/585 |
| 2005/0156604 A1 | 7/2005 | Red'ko et al. |
| 2007/0103150 A1 | 5/2007 | Tada et al. |
| 2008/0143345 A1 | 6/2008 | Boudaoud et al. |
| 2008/0199359 A1 | 8/2008 | Davis et al. |
| 2009/0027070 A1 | 1/2009 | Gelling |
| 2009/0061733 A1 | 3/2009 | Fujita et al. |
| 2009/0079424 A1 | 3/2009 | Tralshawala et al. |
| 2009/0128272 A1 | 5/2009 | Hills |
| 2010/0253371 A1 | 10/2010 | Bierl et al. |
| 2010/0327884 A1 | 12/2010 | McCall et al. |
| 2011/0068807 A1 | 3/2011 | Kesil et al. |

FOREIGN PATENT DOCUMENTS

| | | |
|---|---|---|
| WO | 2008076453 A1 | 6/2008 |
| WO | 2008145188 A1 | 12/2008 |
| WO | 2011038003 A1 | 3/2011 |

OTHER PUBLICATIONS

B. Jeanneret, J. L. Gavilano, G. A. Racine, CH. Leemann and P. Martinoli: "Inductive conductance measurements in two-dimensional superconducting systems", Applied Physics Letters, vol. 55, No. 22, pp. 2336-2338, dated Nov. 27, 1989.

Notification Concerning Transmittal of International Preliminary Report on Patentability (Chapter I of the Patent Cooperation Treaty dated, Apr. 5, 2012 for corresponding International Patent Application No. PCT/US2010/049824.

International Preliminary Report on Patentability, dated Mar. 27, 2012.

Written Opinion of the International Searching Authority for corresponding International Patent Application No. PCT/US2010/049824, 2010.

Notification of Transmittal of the International Search Report and Written Opinion for PCT/US2012/038389, dated Nov. 6, 2012.

The International Search Report for PCT/US2012/038369, 2012.

Written Opinion for PCT/US2012/038369, 2012.

* cited by examiner

IMPEDANCE SENSING SYSTEMS AND METHODS FOR USE IN MEASURING CONSTITUENTS IN SOLID AND FLUID OBJECTS

CLAIM OF PRIORITY

This application claims priority to U.S. Provisional patent Application Ser. No. 61/244,584 entitled "Impedance sensors and their use for analyzing object's compositions" filed Sep. 22, 2009. The above-identified Provisional Application is fully incorporated herein by reference.

STATEMENT REGARDING FEDERALLY SPONSORED RESEARCH

Not Applicable

REFERENCE TO MICROFICHE APPENDIX

Not Applicable

FIELD OF THE INVENTION

This invention relates to a new extremely sensitive kind of electrical sensors that makes possible measurement of physical characteristics, detection and quantification of constituencies of solids, bulk materials and fluids. More particularly, the new sensor technology allows for new real-time non-contact methods for measurement, detection and quantification of components in said materials regardless of its conductivity, transparency and reflectivity under most environmental condition to apply Impedance Resonance Spectroscopy.

SHORT DESCRIPTION OF THE INVENTION

An electrical resonance sensor that can be used in array of similar by design sensors, where each sensor comprises two coils, one of which is excitation coil and the other is sensing coil and in electromagnetic coupling with object under test works at predetermined resonant frequency that was chosen for providing strong correlation of sensor indication with a parameter of interest in radiofrequency range (RF); and the method of using said sensors to measure the physical characteristics and/or composition of the subject under test without contact in real-time.

BACKGROUND

Human society is in continuous search for inexpensive versatile technology that can in real-time without contact monitor numerous technological process, environment, food production, public safety and medical procedures. For example: semiconductor and photovoltaic industries need an advanced process monitoring devices during entire fabrication of Integrated Circuits (IC), flat panel displays and solar panels. Starting from measuring properties of bare wafers and other substrates, monitoring film thickness during various deposition and polishing processes as well as final IC testing requires constant process monitoring and measurements. Agriculture, food, chemical and pharmaceutical industries are interested in sensing technology to monitor different physical characteristics of organic and inorganic materials, liquids and compositions of numerous constituencies within natural limits. This invention is about a new extremely sensitive sensor system that is a core for new measuring method that is applicable to broad range of conductive, semiconductive and dielectric materials.

SUMMARY

In one aspect, the invention provides a resonance type impedance sensor which is a multicoil open-core or air-core inductor, the sensor comprising at least two coils, one coil being an excitation coil connectable to at least one alternating current source with frequency sweep, another coil being a sensing coil connectable to at least one data processing system, wherein upon electrical connection to said current source, the excitation coil propagates an energy to the sensing coil, which generates a probing electromagnetic field and wherein L C R parameters of the sensing coil are capable of providing resonance conditions for measuring of object under test impedance at predetermined frequency. Various embodiments and variants are provided and contemplated.

In another aspect, the invention provides an impedance sensing system for non-contact and non-invasive measuring and analyzing of targeted chemical and physical properties of gaseous, fluid and solid objects comprising: (A) at least one resonance type impedance sensor described above; (B) at least one alternating current source with frequency sweep electrically connected to said at least one excitation coil; (C) said at least one data processing system in communication with said at least one sensing coil, wherein L C R parameters of said sensing coil provides resonance conditions for measuring of object under test impedance at predetermined frequency; and (D) a control system in communication with said alternating current source and said data processing system. Various embodiments and variants are provided.

In yet another aspect, the invention provides a method of measuring chemical and physical properties of an object by a resonance type impedance sensor, the method comprising:

(A) measuring self-resonance frequency and amplitude of said sensor(s);

(B) placing an object under test comprising at least one analyte;

(C) measuring resonant frequency and amplitude of sensor in the presence of said object;

(D) calculating changes in amplitude and resonant frequency induced by electromagnetic interaction between said sensor and object to determine impedance of said object under test; and (E) matching said impedance with predetermined calibration data to determine said chemical or physical properties of said object under test. The preferred impedance sensor is the sensor described in the sensor aspect of the invention.

It is often required nondestructive contactless in-situ measurements and/or control of various multi-compositional fluids (e.g. water, blood, slurries, different solvents, etc.) and its monitoring for metallic, organic and nonorganic contamination. It is a very common task for many technological processes in many industries including: chemical, semiconductor, pharmaceutical, medicine, agriculture, food processing, etc. Proposed systems and methods are able to detect very small changes not only in mono-compositional structures and fluids but also in most of multi-composition materials, multi-layers structure and liquids with dissolved and/or homogenized constituencies.

The present invention is directed to sensing system (apparatus) comprising of one or an array (cluster) of impedance type sensor(s) which is able to create a non-contact probing, primarily by harmonic high frequency electromagnetic fields in an object under test and analyze complex object response to the sensor's probing field.

This invention primarily relates to wide variety sensor systems and methods for measuring physical parameters and/or chemical constituencies and their distribution in targeted composite object: solid, liquid, gaseous or their combination. The invention can be used practically in all industries, including: utilities, agriculture, food, textile, pharmaceutical, photovoltaic and semiconductor, medical devices, chemical and petro-chemical, metallurgy, Homeland Security.

In particular, this invention discloses a structure of novel RF impedance sensing system and sensors for contact-less real-time (in-situ) measurements (analysis) of composition different materials including of thin and thick films and layers during numerous production processes (e.g. PVD, CVD, ECD, CMP, etc.) in Semiconductor, Flat Panel, Photovoltaic and Disk Drive industries, material science, etc. Also, present invention describes a new method and device (apparatus) for testing liquids, solvents and gas analysis in chemical, food processing, Agricultural and other industry fields as well as in testing laboratories.

The sensing system is, actually, scanning an object under test by generating sweeping voltages in the vicinity of pre-selected frequencies. To provide maximum sensitivity and resolution each Impedance sensor is designed to have resonance in presence of the object under test at one of said pre-selected frequencies.

The Impedance sensors are able to monitor number of targeted parameters (characteristic or properties) of the object by measuring object response to the sensor's electromagnetic field variation represented by resonance amplitude (value) change—dV, resonance frequency shift—dFr and in some cases phase angle displacements—d $\phi$ at pre-selected set of frequencies.

Data processing unit is able to compare and analyze statistically filtered reaction of object-sensor complex on Impedance sensor outputs (V, dV, and Fr, dFr and $\phi$, d$\phi$). The data processing unit stores in memory reference data and an algorithm of their usage. The reference data are acquired in process (usually named calibration) of measuring similar objects with known properties. The algorithm correlates the sensor output signals with quantified characteristic(s) of the targeted property and can comprise interpolation, solution of a system of equation, search in lookup tables and etc.

According to present invention the in-situ Impedance sensors may be designed as an air core cylindrical or planar inductors in one group of embodiments and as ferrite core inductors according to an another one. Each of these sensors has at least one winding named as an excitation coil and at least one winding named as a sensing coil. The excitation coil is connected (coupled) to an output of RF sweep generator and provides electromagnetic pumping to resonance circuit represented by sensing coil. The sensing coil is generating probing electromagnetic field, perceiving an influence on said field by object under test and transferring information about the influence to multi-channel measuring and data processing (signal analyzing) system.

The Impedance sensors, RF sweep generator and data processing system are designed to function as a high speed closed loop self-tuning system continuously searching for a resonance frequency of a system (unity) sensor-object complex, calculating and presenting targeted parameters and characteristics of the object in-real time (on-line) mode.

The present invention is believed to have an advantage of high sensitive impedance measurements using electrical resonance circuit and advantage of Electrochemical Impedance Spectroscopy and Dielectric Relaxation Spectroscopy which provide method of defining optimal operating frequencies for impedance measurements.

High sensitivity impedance measurements are achieved by using refined resonance circuit composed of coil only. Target parameters of impedance measurements are active capacitance and capacitive reactance of object under test, so highest sensitivity can be achieved by minimizing, as much as possible, self resistance and self capacitance of sensing coil. Another improvement is using of excitation coil for transferring energy to sensing coil by excluding generator source's impedance influence on sensing resonance circuit.

State of the art assumes using plurality of frequencies for determining chemical and/or physical properties by measuring electrical impedance properties of an object, but nobody mentioned how the frequencies are chosen. The present invention discloses a new advanced approach. To determine an operating frequency for each impedance sensor of the sensing system an impedance spectrometer is used.

The procedure for constructing of composition sensing system is described below:

A) preparing a set of samples with known composition of target constituents that cover possible variations of object under test;
B) determining an electrical impedance spectrum for each of said samples by scanning over a wide frequency range;
C) analyzing of said spectra to find set of frequencies, at which difference between said spectra correlates with change of target constituents portion and said constituents contribute to impedance with different proportion, wherein number of selected frequencies should be at least equal to number of explored constituents;
D) constructing a set of sensors with operating frequencies based on the results of step C;
E) assembling said set of sensors in proximity to object under test;
F) collecting and storing calibration data using set of samples prepared at the step A; and
G) elaborating and implementing a data processing algorithm.

The above described improvements allowed constructing novel measuring sensor with highest possible sensitivity in RF. The FIGS. 17 and 23 illustrate sensitivity scale of traditional and proposed methods. The proposed sensor system and measurement method increased significantly sensitivity over all known electrical methods. The improvement in sensitivity level is different from a case to case dependant on application. For some applications sensitivity improvement could be measured by factors not percentages.

BRIEF DESCRIPTION OF THE DRAWINGS

This invention is described with reference to specific embodiments thereof. These and other features and advantages of the present invention will be apparent to those skilled in the art from the following detailed description of preferred embodiments and with the accompanying drawings, in which.

DETAILED DESCRIPTION

Figure 1:
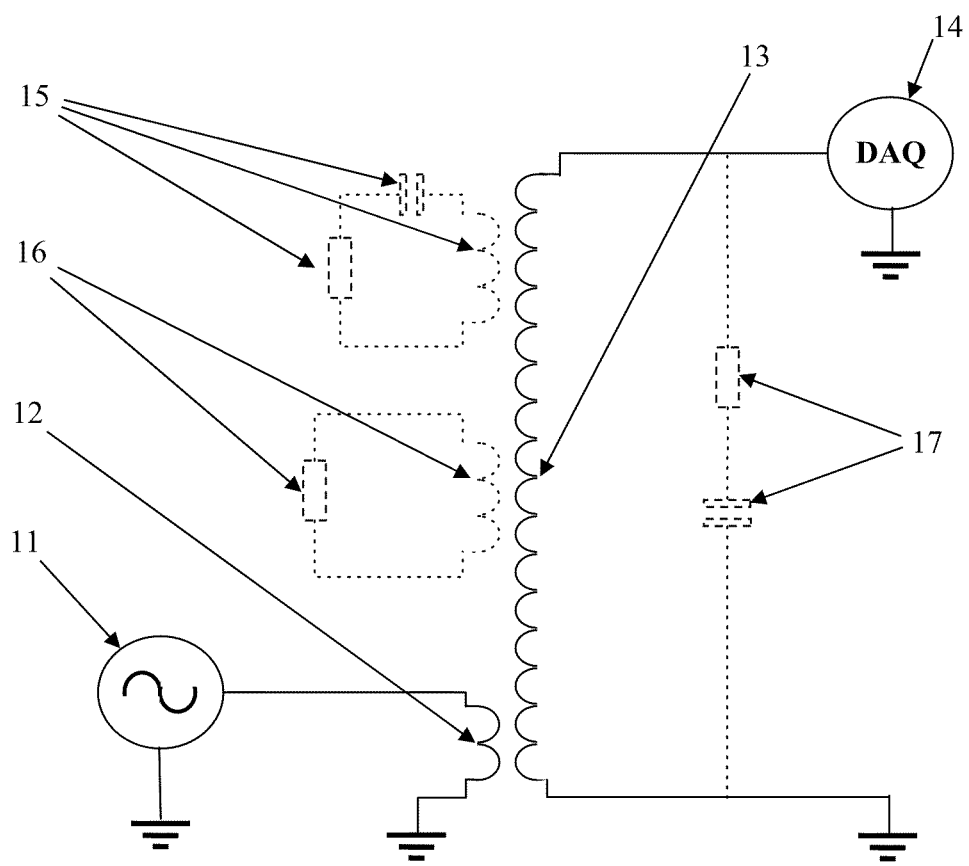
FIG. 1 depicts a simplified equivalent circuit of an Impedance sensor of this invention and object under test response.

Certain patents disclosed apparatus and methods to measure fluid constituencies using electrical resonance circuits. U.S. Pat. No. 7,219,024 describes measurements density and moisture content using electromagnetic probing. U.S. Pat. No. 6,511,851 discloses method for identifying changes in the composition of liquid using resonance frequency circuit. International patent application WO 2008076453 disclosed sensor using its inductor and capacitor for monitoring ethanol/alcohol content of the vehicle engine fuel. United States Patent Application 20080143345 disclosed inductive sensor for automotive urea solution monitoring device deployed in conjunction with the urea tank of a selective catalytic reduction vehicle.

Other patents disclosed apparatus and methods to measure physical and chemical characteristics and their distributions using Electrochemical Impedance Spectroscopy (EIS) and Dielectric Relaxation Spectroscopy (DRS). USPTO Patent Application 20090027070 discloses a dual cell Electrochemical Impedance System (EIS) testing apparatus and method for measuring coating integrity on various substrates. U.S. Pat. No. 4,433,286 discloses identification of materials using their complex dielectric response. U.S. Pat. No. 7,514,938 discloses dielectric relaxation spectroscopy apparatus and method of use, for non-invasive determination of presence or concentration of an analyte in the sample.

There are numerous measuring techniques suggested for measuring thickness, uniformity, composition and contamination of thin and thick layers. Optical methods, like ellipsometry, are common in the semiconductor industry. They are mostly used for measurements of transparent layers. The X-ray technique is expensive, associated with safety issues and has limited application in production lines.

Other methods include AC and DC point probes, capacitive sensors (U.S. Pat. No. 7,332,902), inductive Eddy current technology (US patent publications 200501566042 and 20090079424) and others are dependent on a variety of factors that are difficult to control. Enhancements of Inductive and RF Impedance analyzing methods are disclosed in several patents (e.g., U.S. Pat. No. 6,593,738 and U.S. Pat. No. 6,891,380). Electrically based methods either require electrical connections to the measured thin layer that often affect the measured object or are noncontact, and are slow and have a low sensitivity.

It is believed that the optical methods often cannot be reliably used when measuring opaque or nontransparent layers and stacks of transparent layers. Things are further complicated by optical properties of the measured layers (the index of refraction, extinction coefficient, etc.) and by the surface roughness of the measured and/or underlying layers.

Furthermore, the techniques known in the art are unable to measure thicknesses of targeted individual layer(s) inside composite multi-layer objects with high accuracy. Most of those known techniques are limited by one or a combination of shortcomings such as speed of measurement, optical properties and material's conductivity. In addition, some of these techniques are destructive and/or require a direct contact which is highly undesirable.

Optical, X-ray and existing Impedance spectroscopy devices are bulky, overly expensive and not ready for in-situ type measurements.

While the present invention is not limited to any specific theory, traditionally a sensitive resonance circuit is an electrical circuit composed of at least two elements: inductor and capacitor electrically connected to each other. In order to maximize sensitivity of resonance circuit to electrical impedance of an object under test it was believed to be necessary to minimize capacitance and resistance of the resonance circuit. The inventors have unexpectedly discovered that the traditional electrical circuit, composed of inductor and capacitor, may be replaced by an inductor alone. The said inductor (induction coil) should be coreless or an open core type to serve as sensing element. The sensing coil is a main part of the inductor and its parameters define operating frequency of invented sensor. Sensor's sensitivity can be further increased by using monolayer coil with substantial step between turns or using basket winding to decrease self capacitance of sensing coil.

While the invention is not limited to any specific theory, another significant feature that is believed to have contributed to high sensitivity of the invented sensor is an electrical separation of AC current source from the sensing coil; it is in order to exclude or minimize the influence of source impedance on the sensor's sensitivity. That was achieved by using excitation coil for electromagnetically transferring energy from source of AC current to sensing coil.

Another important aspect of our sensor design that was never introduced in prior art is a requirement for high input impedance of the data processing module. To achieve high sensor sensitivity the input impedance should be extremely high (for example, our data acquisition unit has 10 GΩ input resistance). Correctness of such requirement can be proven by formula:

$$W = V^2/R \text{ where,}$$

W—energy dissipated on input resistance of data acquisition,
V—voltage of useful signal (for our DAQ it is 0.5-11 V)
R—input resistance of instrumentation connected to sensing coil (for example DAQ)

From above formula, it is obvious that energy dissipation is smaller when higher input resistance is used. For example, when we are replacing 10 GΩ DAQ by standard oscilloscope (even with 10 MΩ attenuator) a drastic sink in sensor sensitivity is observed.

There are several patents (U.S. Pat. No. 4,058,766, U.S. Pat. No. 4,433,286, U.S. Pat. No. 6,669,557, U.S. Pat. No. 7,219,024) mentioned use a plurality of frequencies for determining different chemical and physical features of different objects through the measuring electrical impedance, but none of the patent described criteria for defining frequencies in use. Present invention uses phenomenon of changing impedance property with changing of frequency for searching optimal operating frequencies for sensors of composition sensing systems. Information about object's impedance at frequencies, found using impedance spectroscopy, make it possible to built a system of invented impedance sensors to determine composition of liquid solutions, gas mixtures, solid composite objects, multilayer objects or for monitoring changing in such object composition.

FIG. 1 depicts a simplified equivalent circuit of an Impedance sensor of this invention and object under test response. Impedance sensor is depicted with solid lines. It comprised of alternating current source with frequency sweep 11, excitation coil 12, sensing coil 13, and data processing system 14 (e.g., the data processing system 14 may comprise a data acquisition unit ("DAQ") 14 as best seen in FIG. 1).

The excitation coil function is pumping the sensing coil with electromagnetic energy and a separate a sensing resonance circuit from impedance of alternating current source.

Sensitive resonance circuit of this invention consists of sensing coil only and may be described by parameters of this coil: inductance, inter-turn capacitance, and active resistance.

Impedance sensor design according to aspects of the present invention provides a low capacitance value. It can be desirable to reduce capacitance to the lowest possible practical value.

A sensing coil is coupled with high impedance (preferably in the range of about $10^7$ to about $10^{15} \Omega$) input of data processing system.

Analyze of the equivalent circuit of impedance sensor of present invention shows that output current from sensing coil is usually very small (in the range $10^{-6}$-$10^{-14}$ A).

Response of object under test is depicted with dashed lines. Reactions of the object can be represented by three equivalent electrical circuits: 15, 16, and 17.

Alternating magnetic field of sensing coil generates vortex electric field E and this field, in its turn, induces vortex currents of different type.

Figure 2:
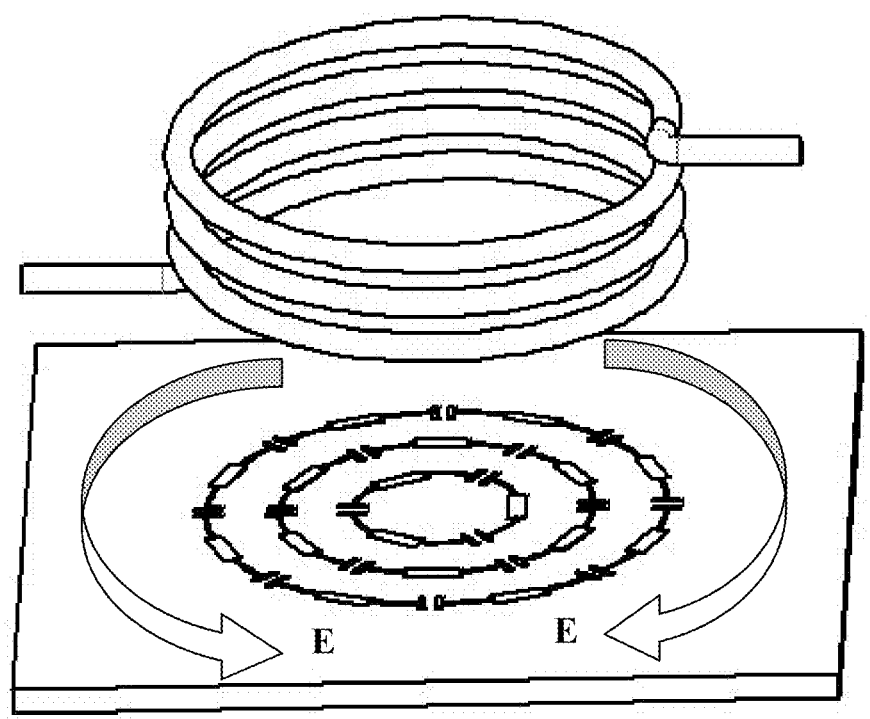
FIG. 2 illustrates response of dielectric object under test to vortex electric field for the object located outside of a sensor.

If a sensing coil is positioned in close proximity to a dielectric solid object, the equivalent circuit 15 consists of resulting parameters L, R, and C. Impedance of circuit 15 reflects resistance to vortex displacement currents generated by vortex electric field E and energy dissipation occurs due to alternating dielectric polarization (FIG. 2).

Figure 3:
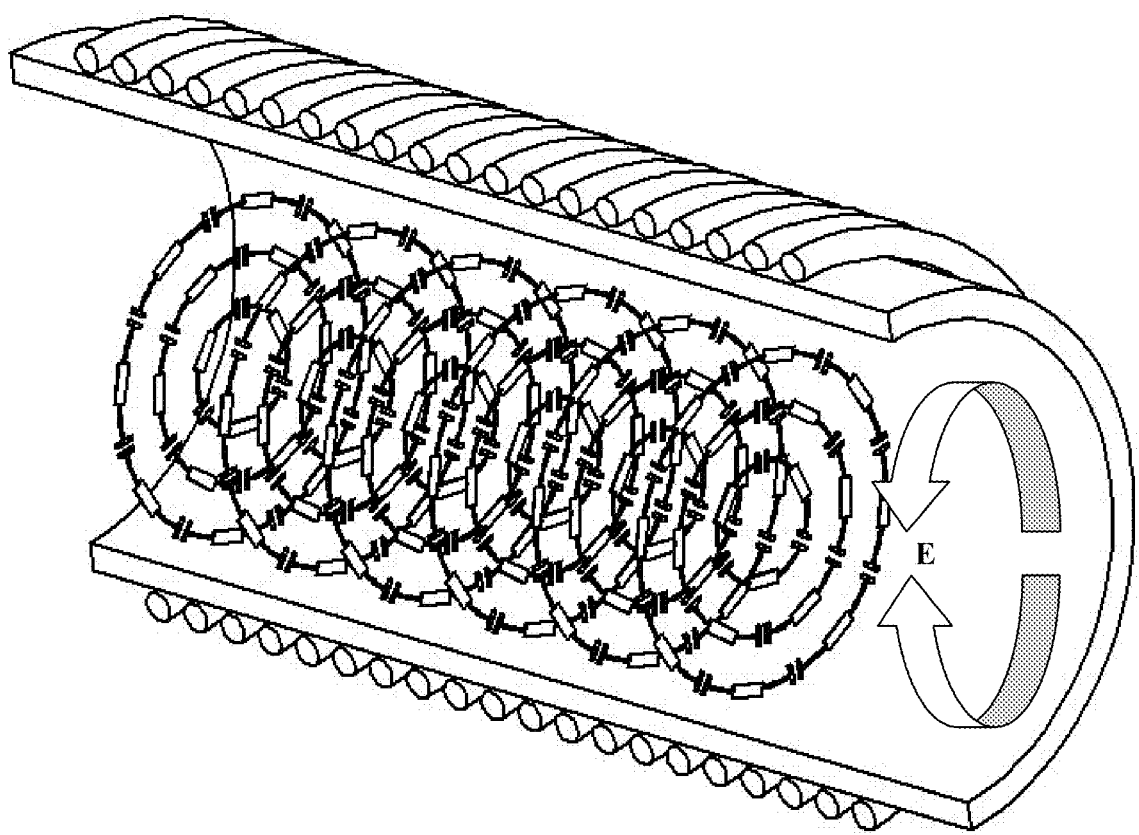
FIG. 3 illustrates response of dielectric object under test to vortex electric field for the object located inside of a sensor.

The same resulting parameters reflect response generated by vortex displacement currents in a tube filled by dielectric fluid. In this embodiment, an object is depicted surrounded by a sensing coil (FIG. 3).

Figure 4:
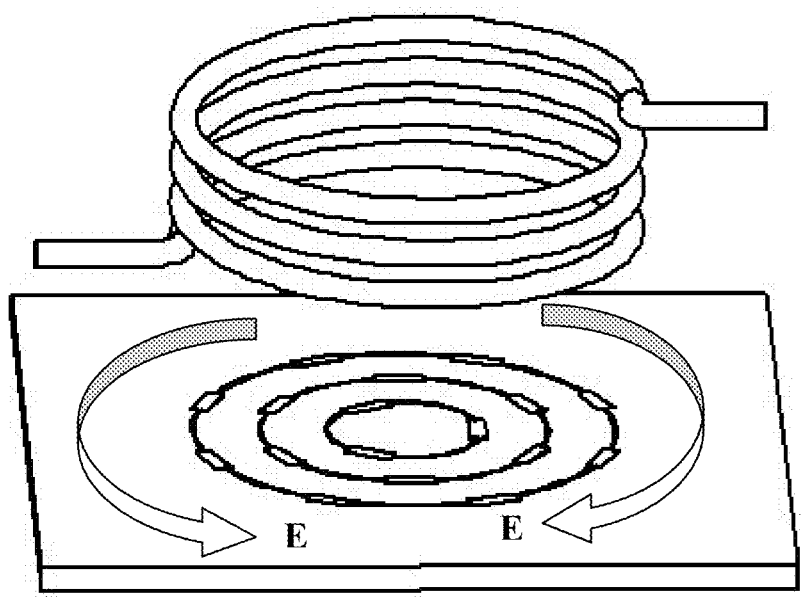
FIG. 4 illustrates response of conductive object under test to vortex electric field for the object located outside of a sensor.

For conductive objects, both solid and fluid, the equivalent electrical circuit 16 can have only two resulting parameters L and R. These parameters consider resistance to both vortex conductive and ionic current flows caused by vortex electric field E and energy dissipation occurs due to eddy currents (FIG. 4).

Figure 5:
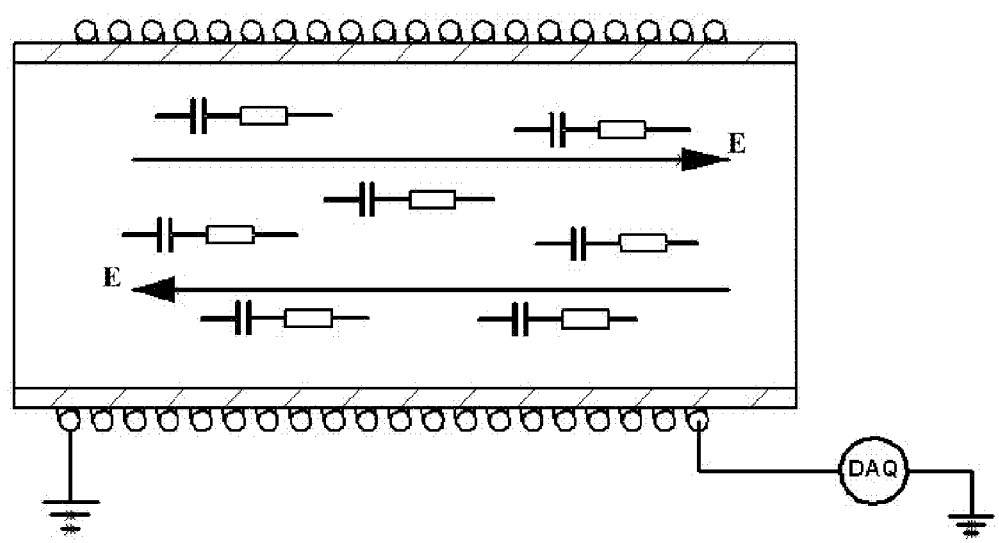
FIG. 5 illustrates response of dielectric object under test to linear electric field for the object located inside a sensor.

Alternating linear electric field E of sensing coil also induces linear currents of different type. Conductive and dielectric objects create capacitive coupling of sensor and object and this relationship is presented by equivalent electrical circuit 17. The impedance reflects an object's resistance to linear conductive currents, displacement currents, or ionic currents generated by a potential gradient in a sensing coil (FIG. 5) or potential difference between coil and object under test (not illustrated).

DESCRIPTION OF EMBODIMENTS

Figure 6:
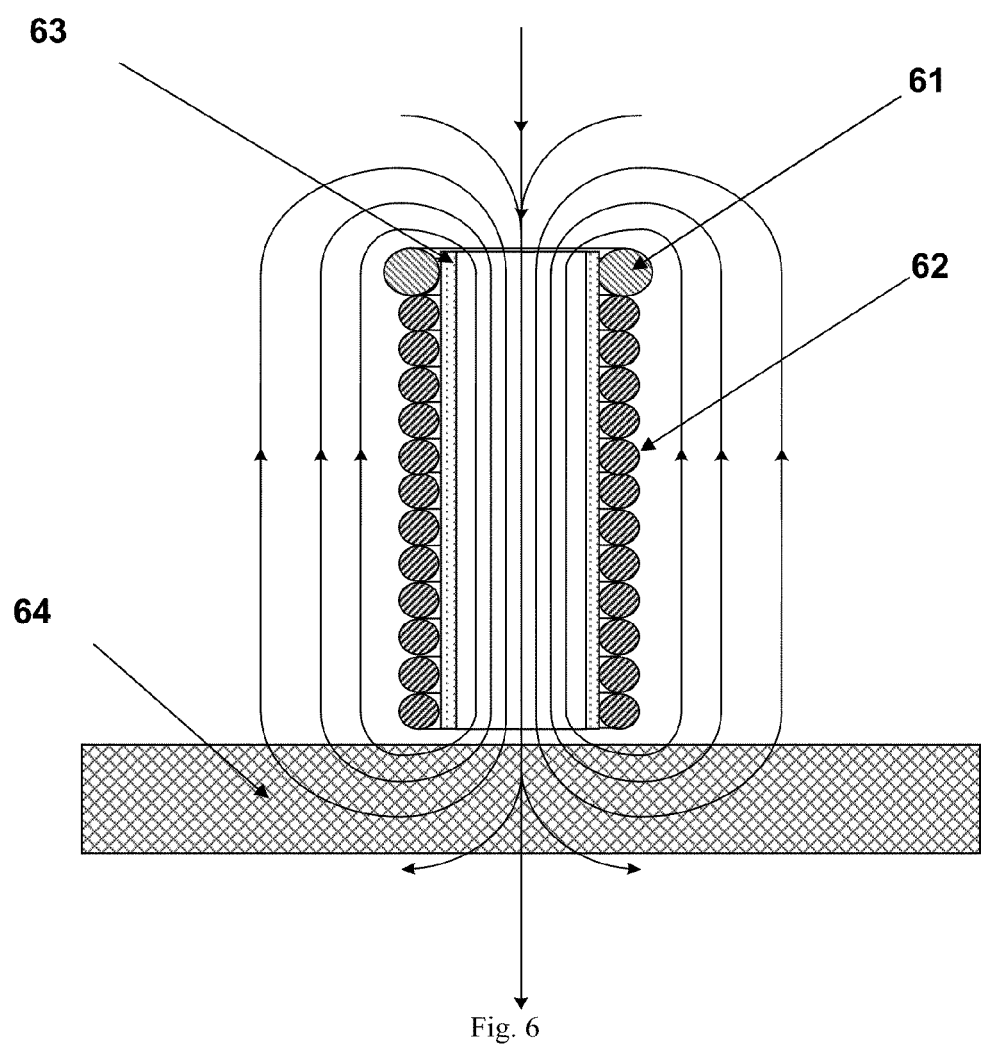
FIG. 6 depicts a sectional view of one embodiment of the impedance sensor (cylindrical type) of the present invention.

Referring now to FIG. 6, that shows a sectional view of one embodiment of the present invention that can be bobbinless or may have a support member 63 which is generally formed as a short tube made from non-conductive material with minimum electrical permittivity (ξ~2) at high RF frequency, such as fluoropolymers. The support member 63 should have thin walls to further minimize sensor capacitance.

The first (upper) section of the support member 63 carries an excitation coil 61 which may have only one or few turns of relatively thick copper wire. One terminal of the excitation coil is connected to ground and second one to low impedance output of RF sweep generator (not shown).

Second section of the support member carries a sensing coil 62. This coil is wound by thinner copper wire than excitation coil. Also, the distance between turns of this coil can be made variable, so the capacitance and inductance of the coil can be mechanically tuned (changed). In this way, the operating frequency of the impedance sensor can be adjusted.

A first terminal of the sensing coil 62 is depicted close to excitation coil 61 and is also connected to the ground. A second terminal of sensing coil is coupled to a high impedance input of multi-channel measuring and data processing system. An end part of the sensing coil 62 is positioned in close proximity to an object 64 under test, which may be solid or fluid. Excitation and sensing coils are wound in opposite directions, so as to obtain the same direction of magnetic field for both coils during transfer energy from the excitation coil to the sensing coil and to provide their electrical separation.

Depending on coils' diameter and number of sensing coil turns the embodiment can have wide range of operating frequencies. The range can be divided in two diapasons: a. operating frequencies <50 MGz that are used for measuring conductive objects and b. operating frequencies 50 MHz-1 GHz that are used for measuring dielectric and semi conductive objects.

Figure 7:
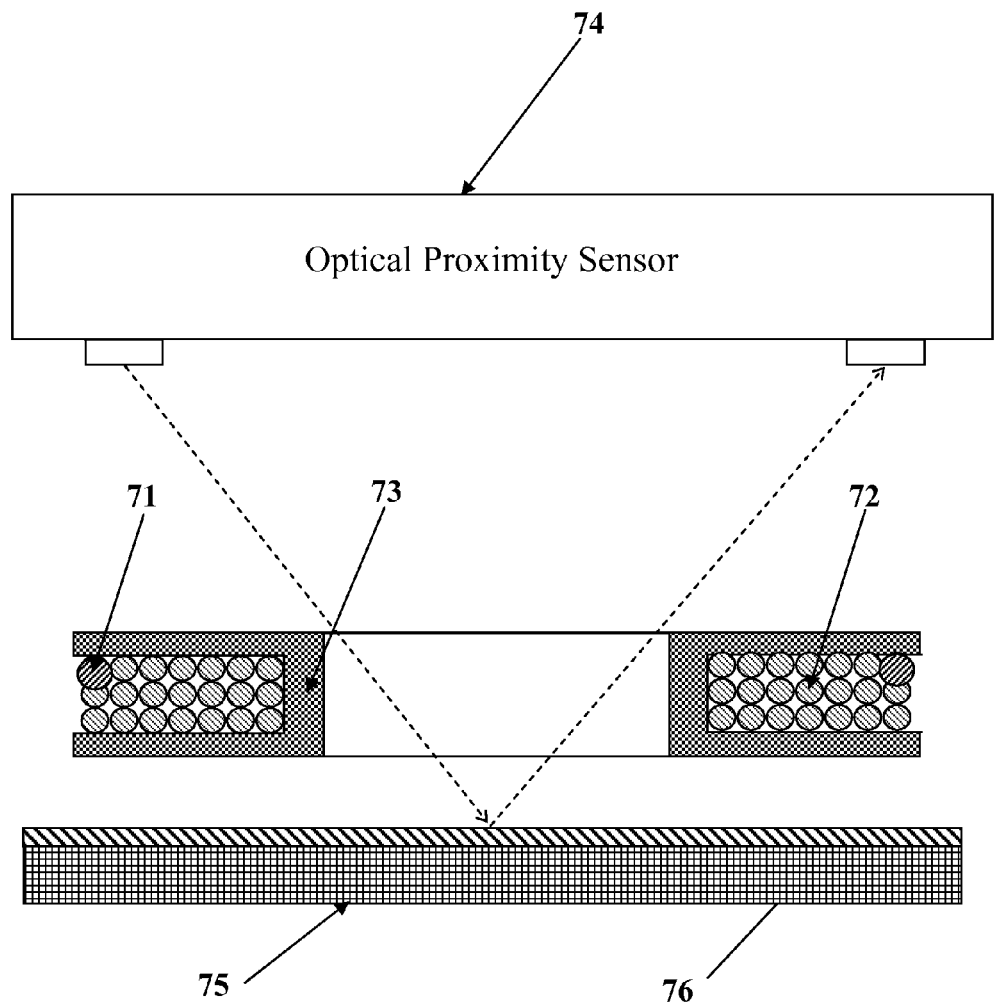
FIG. 7 depicts a sectional view of another embodiment of the impedance sensor (bobbin type) of the present invention.

An alternative support member design for Impedance sensor is shown in FIG. 7. A "bobbin type" support member 73 makes it possible to provide a higher number of turns in the sensing coil 72 and use thinner wire for this coil. Excitation coil 71 has one turn only. The hole in the center of the bobbin is designed for using this sensor with an optical displacement (proximity) sensor 74 to control distance from the coil to film 76 deposited on substrate 75.

There are many applications of present invention related to thickness measurement of thin insulative, conductive and semi conductive layers of wafer, flat panel displays, solar panels, etc. Distance (or gap) between an impedance sensor and targeted layer in the object under test is a critical factor in these cases.

Figure 8:
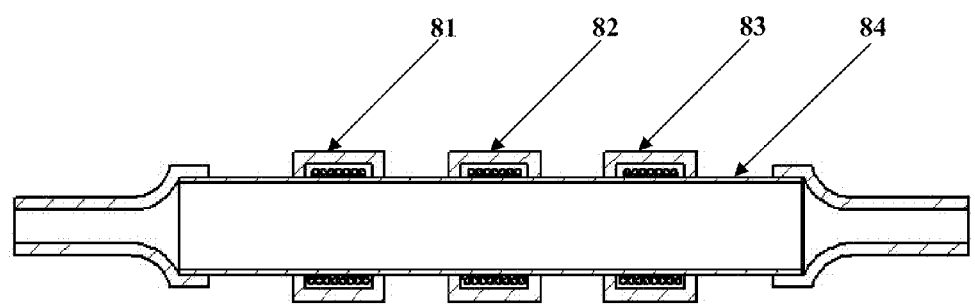
FIG. 8 depicts another embodiment of the present invention for testing flowing in the pipe liquid and comprising an array of Impedance sensors having tree different frequencies.

FIG. 8 depicts a general view of another embodiment of the present invention wherein an array comprising three impedance sensors 81-83 operating at different frequencies. The sensor array of this embodiment is able to monitor at least three constituents in liquids of the interest the same time.

The bobbin-type embodiment with coils of the impedance sensors are installed on sections of pipe 84 carrying a liquid (gas or bulk material) under test. The sensors can be positioned at distances one from other far enough to avoid substantial mutual interference or cross-talk. Also, sensors could operate alternatively. In some embodiments, the distance can be at least equal to or more than the radius of a larger neighboring bobbin.

Each of Impedance sensors in the array in this embodiment has its own (individual) operating frequency specific for each targeted constituent. The sensor array is connected to a controller of the Impedance sensing system (not shown).

Figure 9:
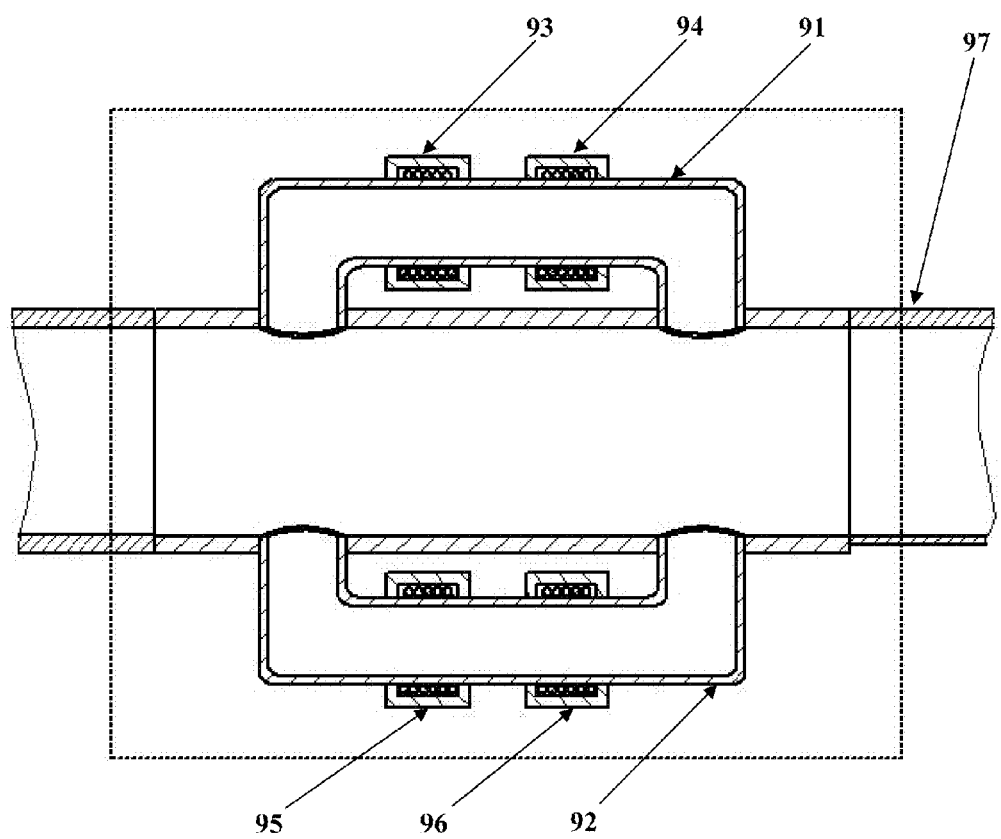
FIG. 9 depicts a general view of another embodiment of the Impedance sensors array of the present invention comprising two bypass sections wherein properties of fluid under test may be monitored by several different impedance sensors (the bypass section can be periodically empty for calibration and correction for wall deposit).

FIG. 9 depicts a sectional view of another embodiment of the present invention wherein a sensor array monitoring flowing fluid (e.g. a liquid) which has included therein constituents of interest. The fluid is flowing through a large diameter dielectric pipe (e.g., 3" or more) or conductive pipe 97 of any diameter. The impedance sensors 93, 94, 95, and 96 are mounted on two smaller bypassing pipes, 91 and 92, (number of bypasses could vary) whose diameters can be configured depending on the application. Each of the sensors has its own resonance frequency specific for each targeted constituent of interest.

This embodiment shows an advantage of using bypass tubes whose diameters match to the optimum diameter of impedance sensor coils (inductance/operating frequency) required for measuring targeted constituent. Also, bypass tubes help by providing suitable distances between sensors working in a close resonance frequency range. Cross-talk and interaction between several impedance sensors can be minimized in this embodiment.

The bypasses can incorporate open and close valves to allow periodic maintenance including calibration and cleaning wall deposits.

Figure 10:
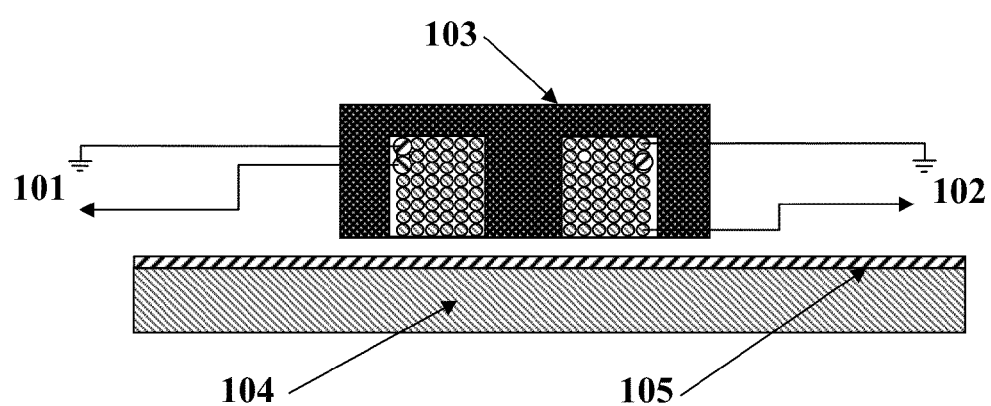
FIG. 10 depicts a sectional view of another embodiment of the impedance sensor (ferrite pot type) of the present invention for measuring solid object.

FIG. 10 depicts a sectional view of another embodiment of the present invention in which both excitation coil 101 and sensing coil 102 are placed inside of a ferrite half-pot 103. In this embodiment, an impedance sensor may be positioned in close proximity to the object 104 under test (e.g., like a substrate with deposited metal layer 105). The ferrite pot in this embodiment is open to the object and provides high magnetic flux to the object under test.

In further embodiments, other shapes of the ferrite cores, such as single "I", "C" or "U" or "E" shapes may be used depending on application requirements. In any case, ferrite cores can increase sensitivity of an impedance sensor, especially, working with conductive and low resistivity objects.

Figure 11:
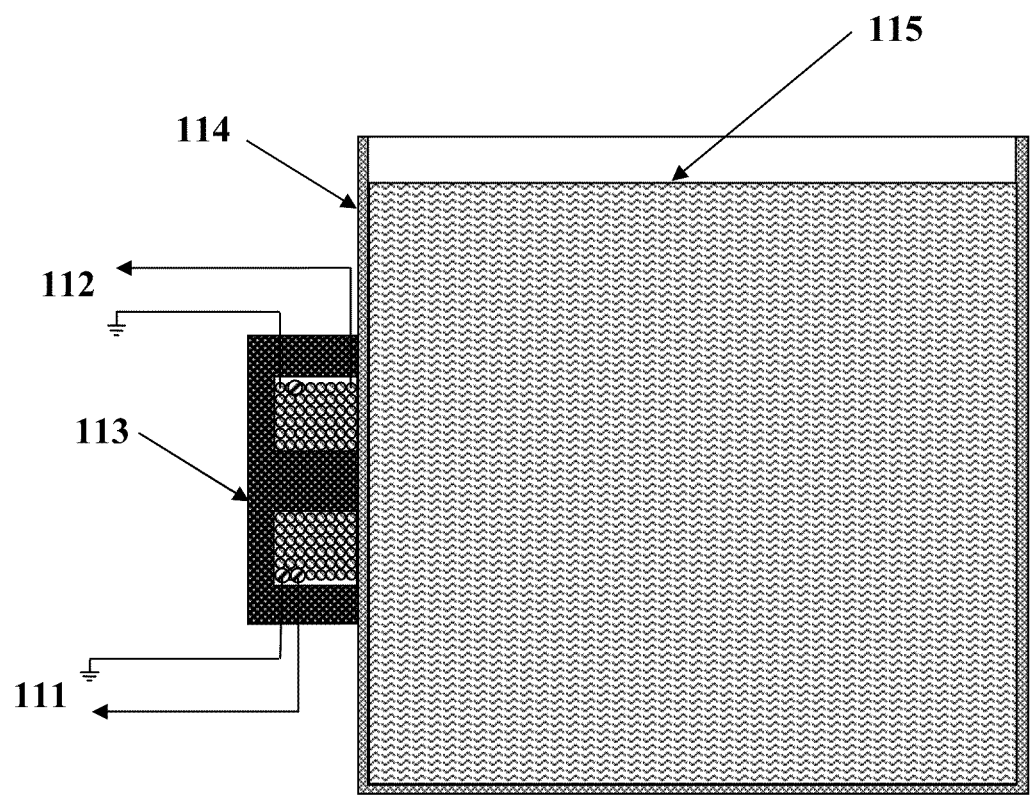
FIG. 11 depicts a sectional view of another embodiment of the impedance sensor (ferrite pot type) of the present invention for measuring liquids and bulk materials.

FIG. 11 depicts a sectional view of another embodiment of the present invention in which sensor is the same as on FIG. 10, but mounted on the wall of vessel 114, which can contains liquid state or bulk material object under test 115. The sensor comprises excitation coil 111 and sensing coil 112 are placed inside of a ferrite half-pot 113.

Figure 12:
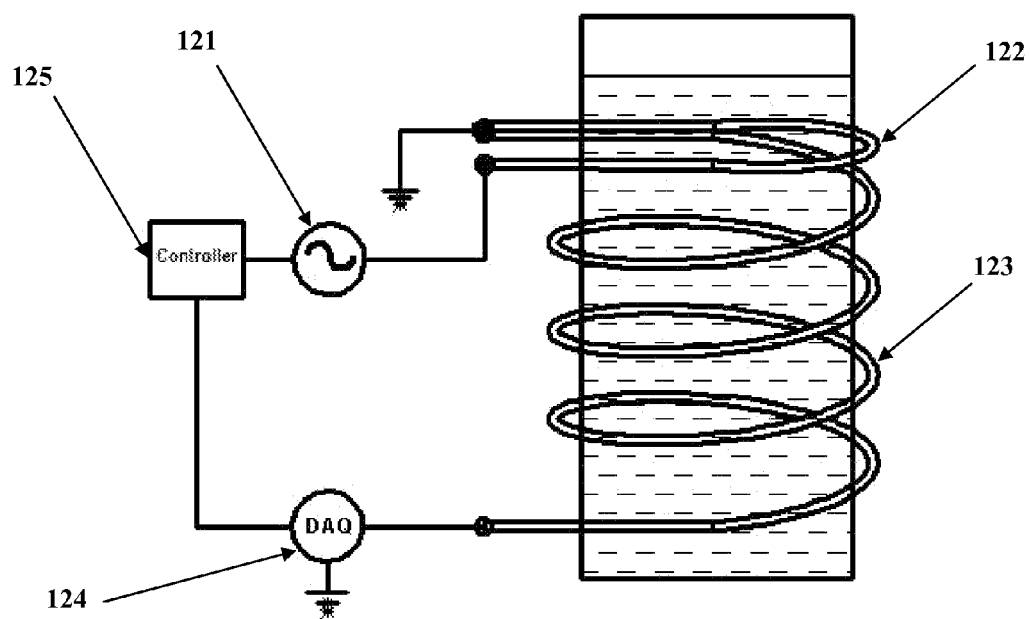
FIG. 12 depicts an embodiment of non-contact sensor device of this invention for measuring liquids and bulk materials with excitation and sensing coils embracing object under test.

FIG. 12 depicts an embodiment of a vessel type, non-contact sensor device of this invention (with excitation and sensing coils embracing object under test) for measuring liquids, gases and bulk materials. This device consists of controllable RF sweep generator 121, excitation coil 122, sensing coil 123, data acquisition 124 (i.e., DAQ or data acquisition unit 124), and controller 125 with data processing system (e.g., the data processing system may include the DAQ 124 as best seen in FIG. 12).

Figure 13:
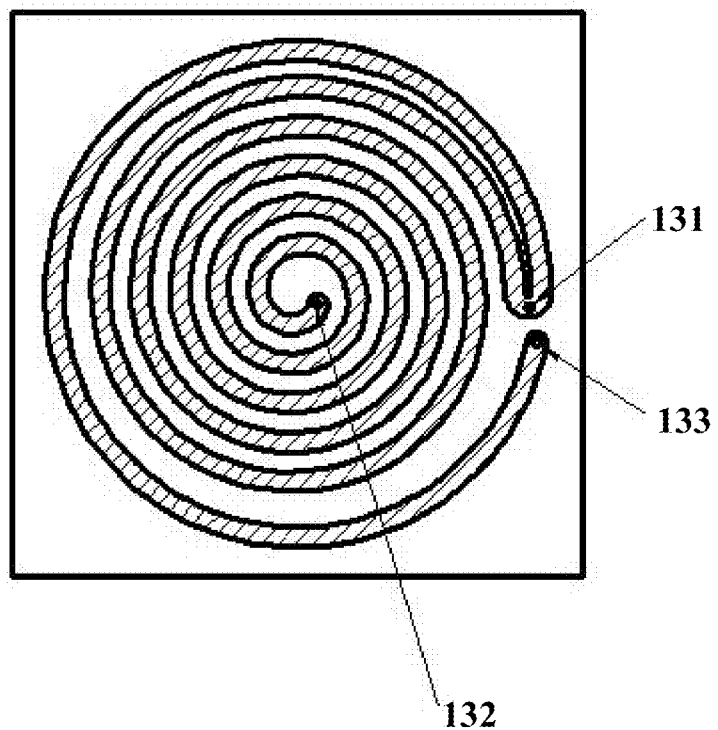
FIG. 13 depicts a general view of an embodiment of a planar sensor of the present invention.

FIG. 13 depicts a general view of another embodiment of the present invention wherein an impedance sensor is configured as two concentric planar inductors. An inner inductor is a sensing coil with many turns where one terminal 131 is grounded and a second terminal 132 can be connected to the controller (not shown). An outer inductor can be an excitation coil grounded from one side 131 and connected to an alternating current source with frequency sweep at other side 133.

A planar impedance sensor can be made by lithography method with both inductors deposited on solid rigid or flexible isolative substrate. This sensor design has several advantages like small size, simple mounting (attaching) to objects like pipe and low cost.

Figure 14:
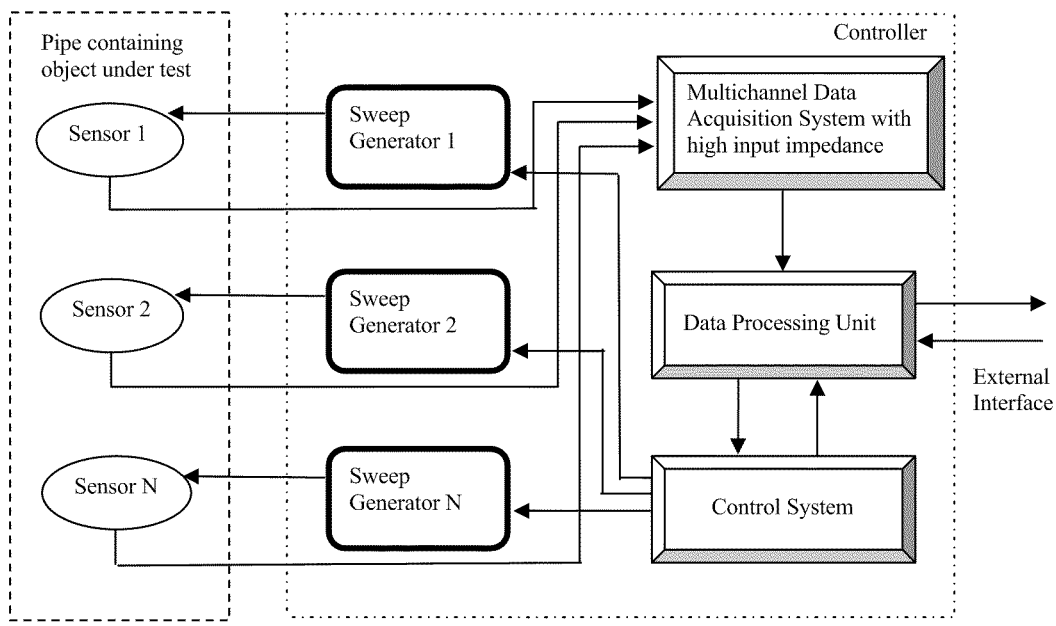
FIG. 14 depicts a block diagram of the sensing system according to the present invention.

FIG. 14 depicts another embodiment of the present invention in which an array of N impedance sensors is connected to a system controller. FIG. 14 depicts a simplified block diagram of a sensing system with controller of this invention.

Excitation coils (not shown) of each impedance sensor are connected to outputs of a required number of RF sweep generators (RFG). The sensing coils of each sensor are connected to high impedance inputs of a multi-channel data processing system (MDS) in the controller.

Both RFG and MDS are connected to a control system that manages information exchanges, scanning, test—measuring presentation of results and other functions. The control system may have several optional correction sensors (e.g., those used to monitor ambient air and/or fluid temperature, humidity, and the like). A controller also may have an interface module to send and receive signals (information) from a higher level tool controller, machine or production floor system.

Real time measurement results may be displayed by controller and/or used as feedback signals for an automated closed loop tool or machine control system. This way the targeted parameter(s) of an object under test may be automatically controlled and maintained within technologically required limits.

Voltage/current output of the RFG can be adjusted depending on electrical and physical properties of the object under test. For example, for measuring the thickness of a conductive metal film, higher excitation coil current/voltage provides increased sensitivity and resolution of the sensing system.

Data processing system can analyze information from RFG, sensors S1 to SN and the control system. The results define specific Resonance Frequency Fro and voltage amplitude Uo for each "object-sensor" system. Based upon this information and calibration algorithms the MDS (Multichannel Data processing System) made conversion of values Fro and Vo in measurement units of the targeted physical or chemical parameters like film thickness, liquid constituencies concentration, layer permittivity and so on. This conversion for two parameters may be illustrated by next system of equations:

$$\begin{cases} X \times k11 + Y \times k21 = Fro \\ X \times k12 + Y \times k22 = Uo \end{cases}$$

Where X is the first targeted parameter (like film thickness), Y is the second parameter (like wafer bulk conductivity), k11 and k12 are frequency weight coefficients, k21 and k22 are output voltage weight coefficients.

The coefficients k11, k21, k12 and k22 are usually found by using a calibration method and then can be retrieved from the MDS memory where they are regularly stored. Calibration procedure comprises measurements of reference samples having known values of targeted parameter(s) and calculation statistically meaningful weight coefficients using acquired data.

EXAMPLES

The following examples are intended to illustrate different applications of this invention, and are not intended to limit the scope of this invention. Persons of ordinary skill in the art can use the disclosures and teachings of this application to produce alternative embodiments without undue experimentation. Each of those embodiments is considered to be part of this invention.

Example 1

Figure 15:
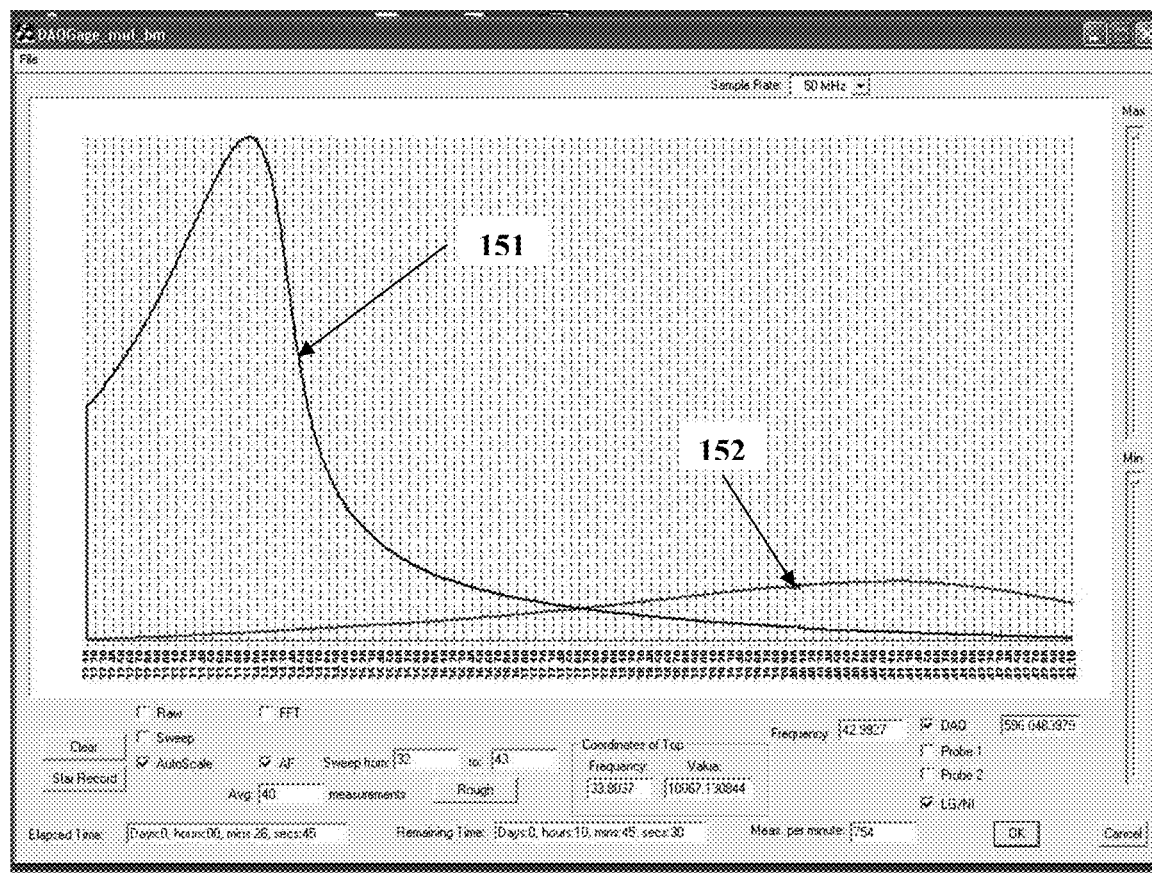
FIG. 15 depicts scope screen shot of output signals of an impedance sensing system of the present invention for a bare silicon wafer and for the same silicon wafer covered by 5000 Å thick aluminum film.

Test on Bare Silicon Wafer and on the Same Wafer Covered by 5000 Å Thick Aluminum Film FIG. 15 depicts a scope screen shot of output signal 151 of an impedance sensor over a range of frequencies 32 MHz to 43 MHz in presence of bare silicon wafer. The resonant frequency is 33.8 MHz, the resonant amplitude is 10067 mV. Line 152 is the amplitude frequency curve for the same impedance sensor in presence of the same silicon wafer covered by 5000 Å thick aluminum film. In this case, the resonance frequency is 41 MHz and the resonant amplitude is 1673 mV. Comparison of lines 151 and 152 shows, that the resonance frequencies and particularly the voltage amplitudes are very different. This example illustrates the high sensitivity of the novel impedance sensing system according to present invention.

Example 2

Test on Samples of Distilled and Tap Water

Test fixture for calibration and measurement variable concentration of different constituencies in liquid (water as an example) shown in FIG. 14, where impedance sensor embraces small vessel-sampler, which is preferably made from Teflon.

Figure 16:
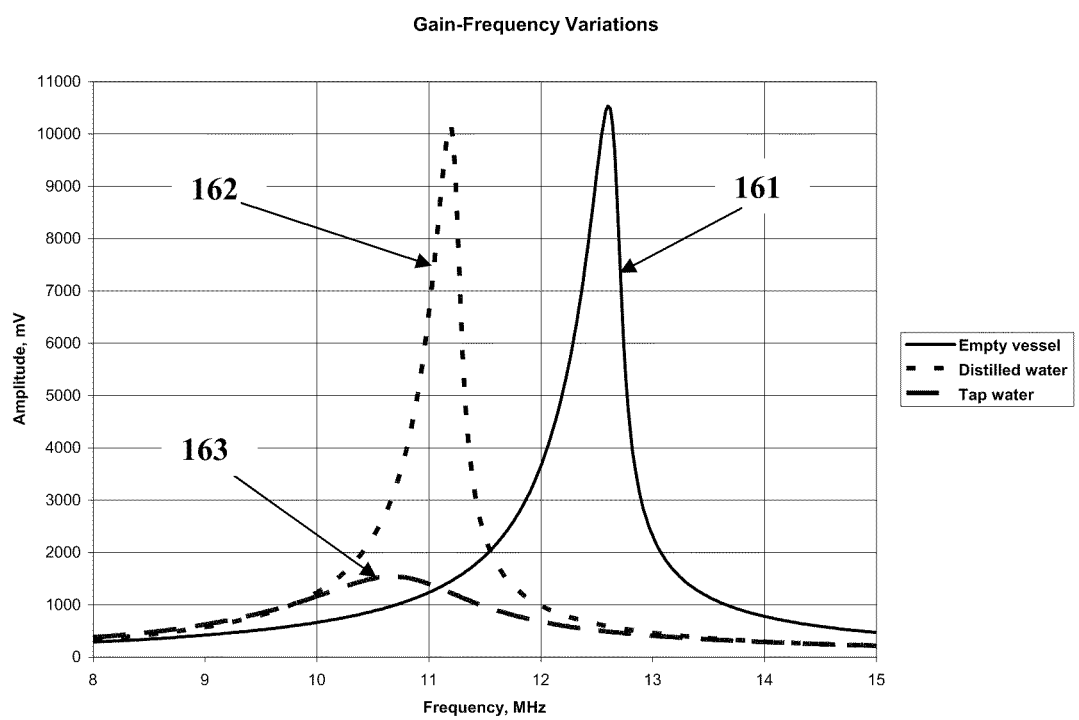
FIG. 16 depicts a graph illustrating test results of a sensing system of the present invention for samples of distilled water and tap water.

FIG. 16 depicts a graph of the test results at different conditions: 161—when there was no liquid in the sampler, 162—when the sampler was filled with distilled water, and 163—when sampler was filled with tap water. The distilled water compared with the empty sampler showed only relatively small change in the output amplitude of the sensor. There was larger shift in resonance frequency from 12.5 MHz for the empty vessel compared to 11 MHz for distilled water. However, the tap water drastically changed both amplitude and resonance frequency. This result is understandable because resistively of distilled water at 25° C. is about 18.2-40 MΩ-cm and tap water is usually below 0.1 MΩ-cm.

This Example demonstrates a very high sensitivity of the novel impedance sensing system and indicates that even small contamination of a liquid object can be detected and quantified.

Example 3

Measuring Different Concentrations of NaCl in Water

To determine proper working frequencies for solutions of sodium chloride (NaCl) in water, preliminary studies were carried out by probing the harmonic electromagnetic field over a wide range of working frequencies: 20 MHz, 70 MHz, 370 MHz, and 480 MHz. Frequencies in vicinity of 20 MHz showed the better results.

Figure 17:
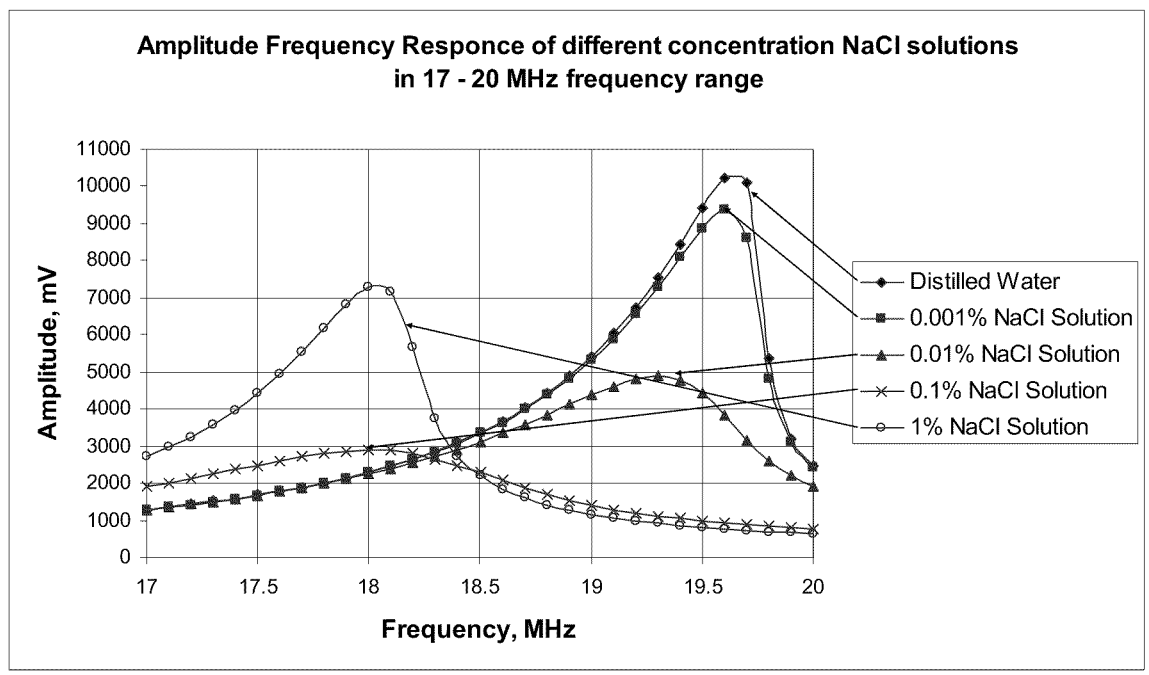
FIG. 17, FIG. 18, and FIG. 19, depict graphs illustrating test results of a sensing system of the present invention for samples of distilled water and water having different concentrations of sodium chloride (NaCl) in the frequency range of 17-20 MHz.

The frequencies in the range of 17 to 20 MHz were chosen for an impedance sensor. In the next example, the amplitude-frequency response was measured for different concentrations of NaCl. FIG. 17 depicts a graph of results of these measurements. As can be seen from the graph of the amplitude-frequency curve, solutions containing different concentrations of NaCl are clearly distinguishable from each other. Distilled water (filled diamonds) produced the highest amplitude at a frequency of about 19.6 MHz, the lowest concentration of NaCl produced amplitude less than that of distilled water, and with increasing concentrations of NaCl, the amplitude decreased, and the frequency of the maximum amplitude decreased until a concentration of 0.1% was achieved. Also, clearly shown is the finding that a 1% solution of NaCl produced amplitude greater than that observed for the next lower concentrations. These results demonstrate the ability of the novel impedance sensing system to measure a wide range of concentrations of liquid constituencies with high resolution.

Figure 18:
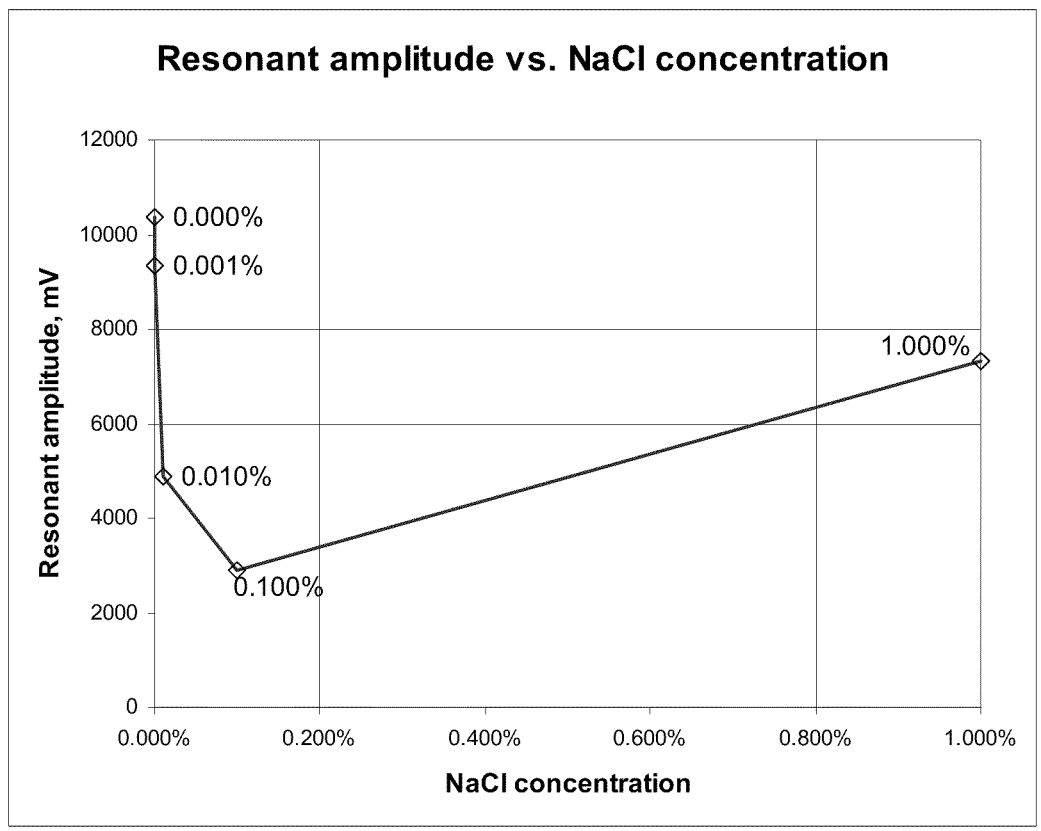
Figure 19:
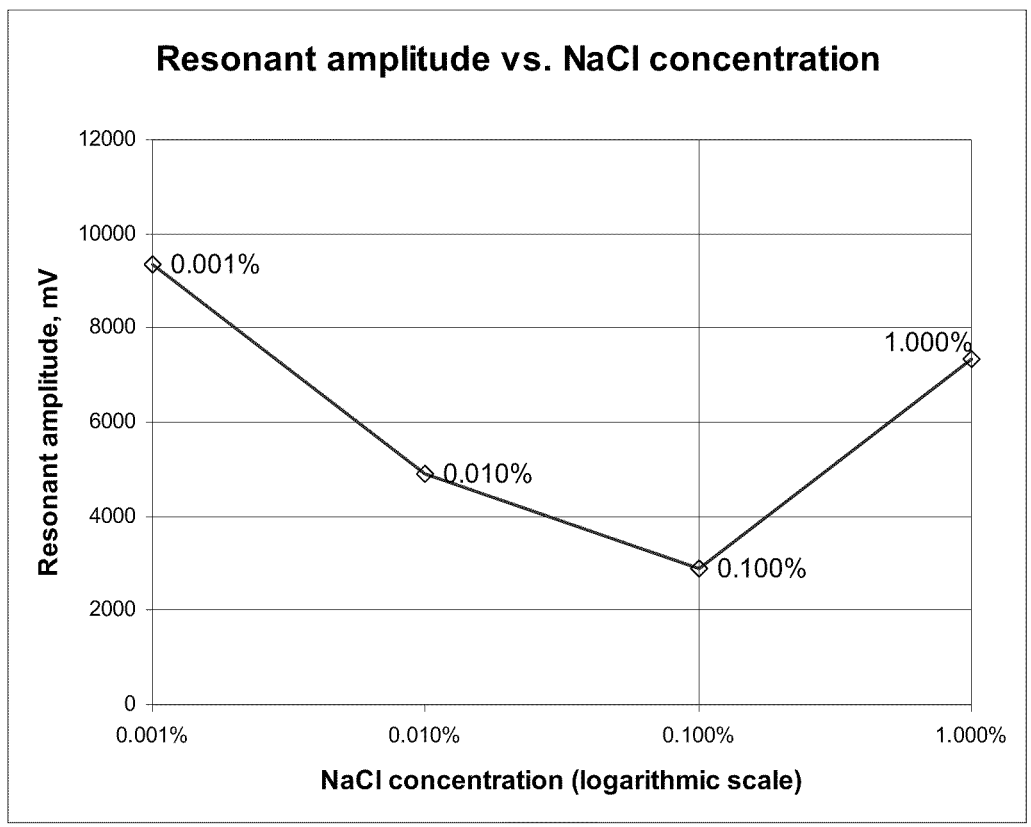

FIG. 18 depicts dependence of impedance sensor's resonant amplitude when concentration of NaCl is measured. FIG. 19 depicts the same dependence when NaCl concentration is represented in logarithmic scale.

Example 4

Measurement of Thickness of Thin Aluminum Films on Silicon Wafers

Figure 20:
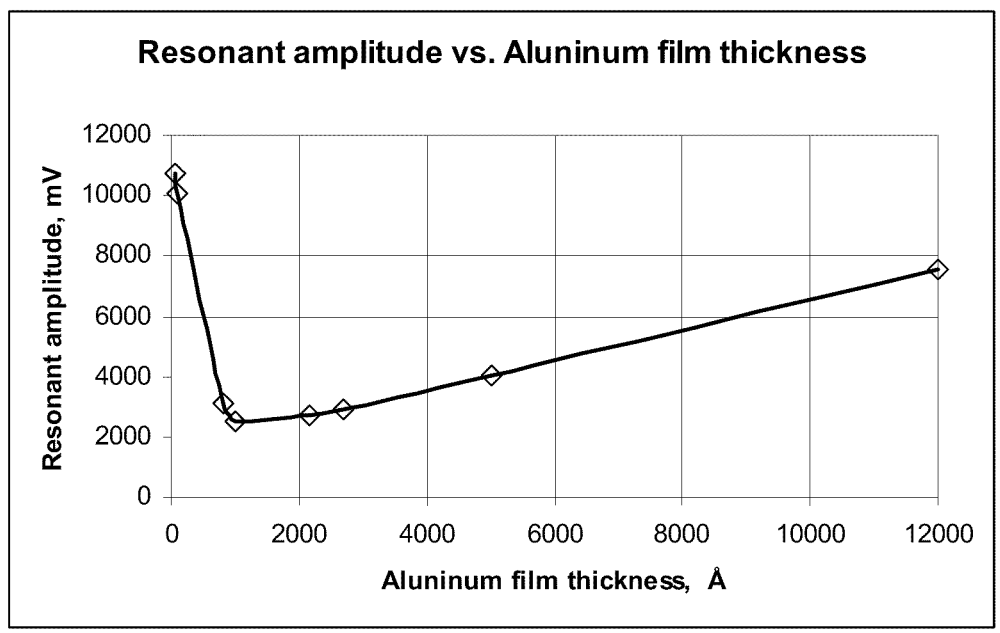
FIG. 20 and FIG. 21 depicts graphs illustrating test results of measurements with sensing system of this invention for silicon wafers having different thicknesses of aluminum film.

FIG. 20 presents tests results of aluminum film thickness measurement (depicted in the Angstroms range). A sensing system used an open core resonance sensor similar to shown in FIG. 7. Frequency range was set from 34 MHz to 43 MHz. The start point in the plot corresponds to a bare silicon wafer with no aluminum film.

Figure 21:
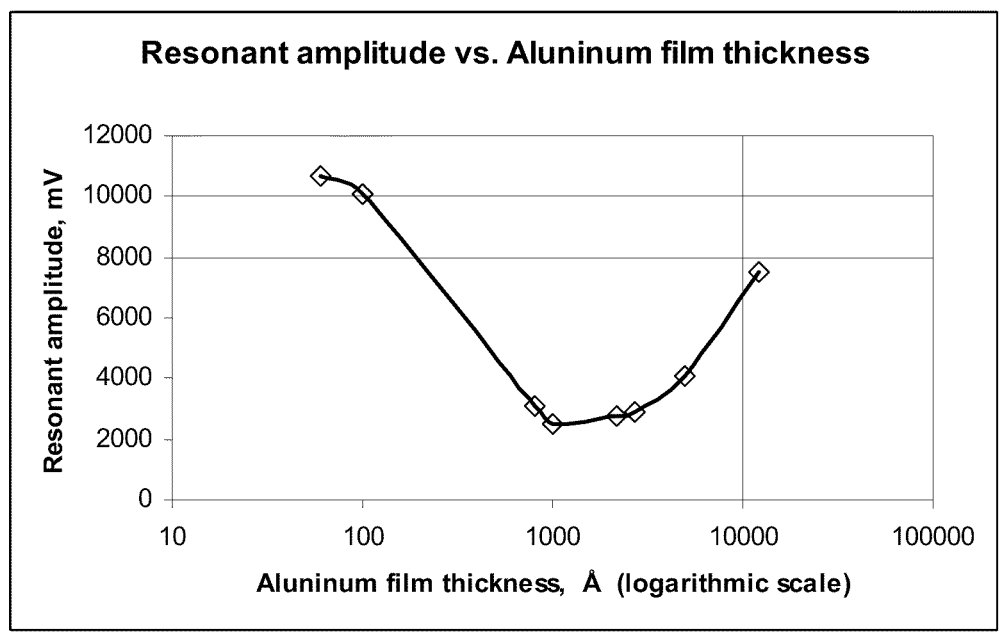

FIG. 21 depicts the same results where aluminum film thickness is represented in logarithmic scale.

Example 5

Measurements of Mercury in Water

One of the most dangerous contaminants in drinking water is mercury. This contamination is highly topical even at very small concentrations. Therefore, we carried out a series of experiments to measure mercury (Hg) concentrations in water.

In one group of experiments, the frequency range was found at which concentration of ions of mercury (Hg+) in distilled water make a significant change in the amplitude-frequency characteristic. This frequency defines L, C and R reference values for a coil design. The measuring coil can be constructed per well known design rules with consideration of the particular lay-out. Also, to achieve maximum sensitivity, it can be desirable to maintain self-capacitance C at minimum for the measuring circuit. The next experiments were conducted with the above mentioned sensor.

Figure 22:
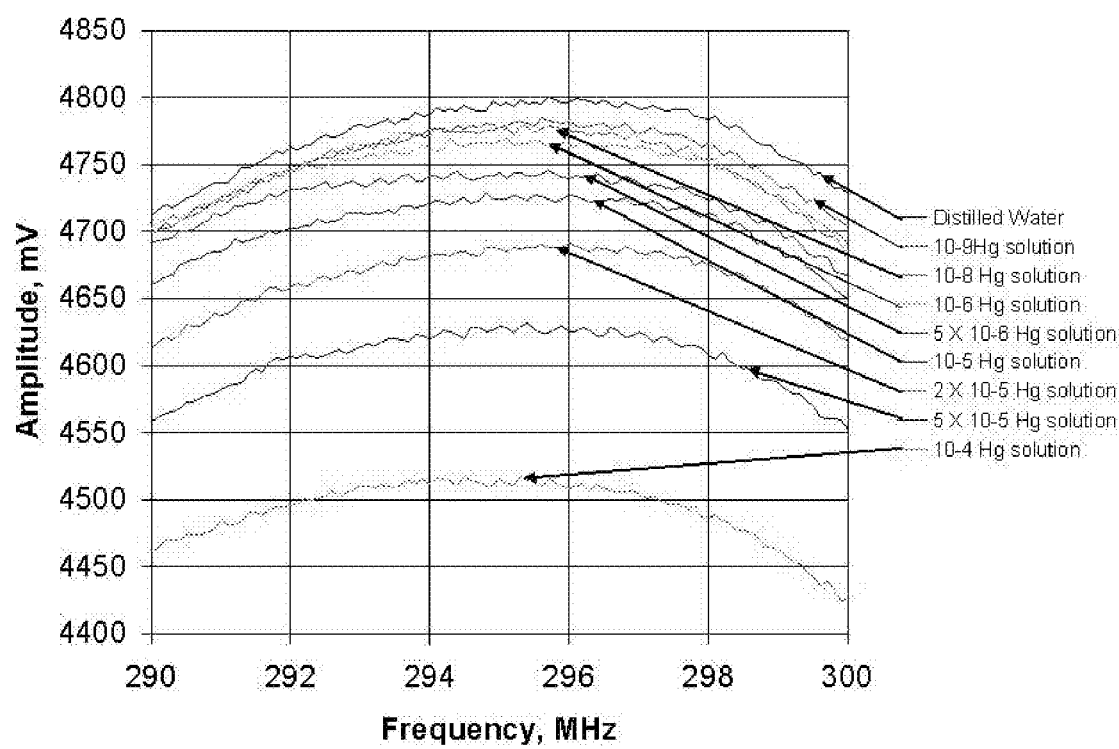
FIG. 22 depicts a graph illustrating test results of a sensing system of the present invention for measuring mercury contamination in water.

FIG. 22 is a graph depicting amplitude-frequency characteristics (AFC) for samples with different concentration of Hg+ in distilled water. Test results clearly demonstrated the ability of an impedance sensing system of this invention to measure Hg+ concentration in distilled water at levels as low as 1 ppb (part per billion).

Example 6

Decreased Sensitivity of IRT-Sensor if Resonant Circuit Includes a Capacitor

To confirm our conclusion from the above of the role of capacitance of an impedance resonance device in modulating the amplitude-frequency relationships of an embodiment of this invention, we carried out a series of studies using solutions of NaCl, as described in Example 3, but in which the resonant circuit of the device includes a capacitor.

Figure 23:
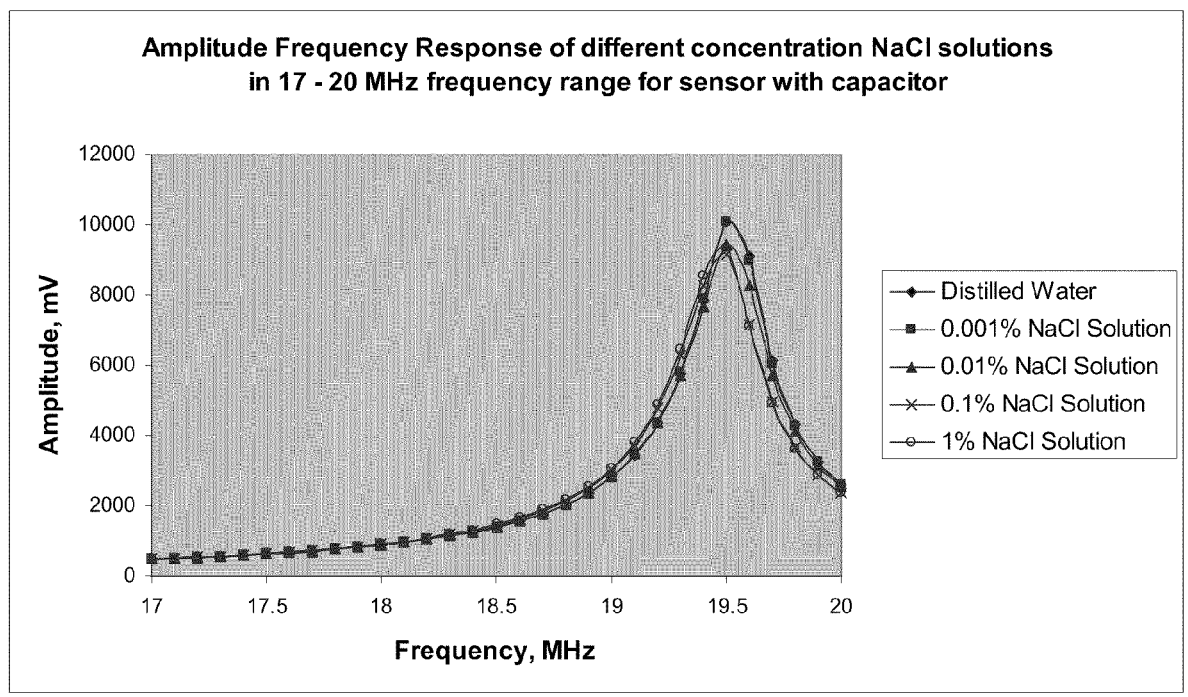
FIG. 23 depicts a graph of amplitude/frequency response curves for solutions of water containing different concentration NaCl in the frequency range of 17-20 MHz for a sensor of this invention with a 20 pF capacitor.

FIG. 23 depicts a graph of amplitude frequency response (AFR) curves obtained using an IRT-sensor which has approximately four times fewer winds than the sensor in Example 3 and with the addition of a 20 pF capacitor. Using this modified sensor with the added capacitor, we found, quite expectedly, that the amplitude-frequency relationships for each of the NaCl solutions were nearly identical, with a noted absence of change in either the amplitude or the frequency at which the maximum amplitude was observed.

Figure 24:
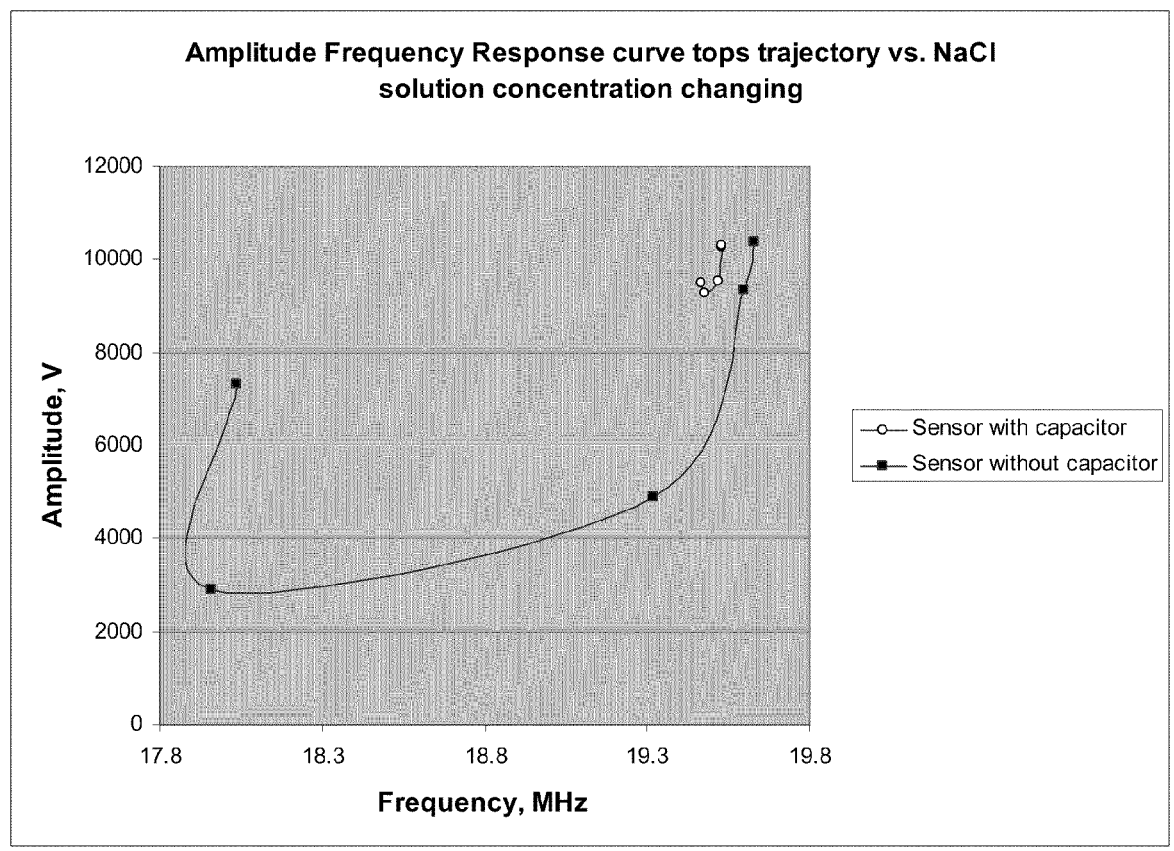
FIG. 24 depicts maxima of amplitude/frequency response curves as a function of the concentration of NaCl in water for embodiments of this invention having a 20 pF capacitor and for a sensor system without added capacitance.

FIG. 24 depicts maxima of Amplitude Frequency Response curve's for sensors with and without the added capacitor. As it can be distinctly seen, embodiments having added capacitors (open circles) have a substantially narrower range of useful signals (resonant frequency and amplitude variation) compared to sensors without added capacitors. In contrast, according to theory, we found that impedance resonance sensor systems without the added capacitance showed a very wide range of useful signals.

This Example demonstrates that systems and methods of this invention have substantially greater sensitivity than prior art sensing systems. Therefore, use of systems and methods of this invention can provide those responsible for maintaining products free of unwanted contamination.

We claim:

1. A resonance type impedance sensor which is a multicoil open-core or air-core inductor, said sensor comprising at least two coils, at least one coil of the at least two coils being at least one excitation coil connectable to at least one alternating current source with frequency sweep, at least one other coil of the at least two coils being at least one sensing coil connectable to at least one data processing system and/or data acquisition unit ("DAQ"), wherein: (i) upon electrical connection to said current source, said at least one excitation coil is capable of propagating an energy to said at least one sensing coil, which is capable of generating a probing electromagnetic field, (ii) said at least one sensing coil is designed in such a way that intrinsic inductance L, capacitance C, and resistance R parameters of said at least one sensing coil are capable of providing resonance conditions for measuring of object under test impedance at a predetermined frequency or at a predetermined frequency range; and (iii) said at least one sensing coil uses only its intrinsic (distributed) capacitance and is not connected to any capacitance means such that said at least one sensing coil is capable of measuring at least one of conductance, conductivity and one or more dielectric properties of at least a part of said object under test being disposed within a sensing area of said at least one sensing coil.

2. The sensor of claim 1, further comprising: (i) said at least one alternating current source with frequency sweep electrically connected to said at least one excitation coil; and (ii) said at least one data processing system and/or DAQ in communication with said at least one sensing coil, where said L C R parameters of said at least one sensing coil provide resonance conditions for the measuring of the object under test impedance at the predetermined frequency or at the predetermined frequency range.

3. A method of measuring chemical and physical properties of an object by at least one resonance type impedance sensor of claim 1 or of claim 2, said method comprising:
   (A) measuring a resonant frequency (self-resonance frequency) and amplitude of said sensor(s) in the absence of an object under test;
   (B) placing an object under test comprising at least one analyte in close proximity of said sensor(s) in order to provide penetration of said electromagnetic field induced by said sensor(s) into said object under test;
   (C) measuring a resonant frequency and amplitude of sensor(s) in the presence of said object;
   (D) calculating changes in amplitude and resonant frequency induced by electromagnetic interaction between said sensor(s) and object to determine impedance of said object under test; and
   (E) matching said impedance with predetermined calibration data to determine said chemical or physical properties of said object under test.

4. The method of claim 3, further comprising monitoring of time-related changes in impedance and correlating said chemical or physical properties of said object under test to said time-related changes in impedance.

5. The method of claim 3, further comprising applying additional external influence(s) on said object under test to improve sensitivity of said at least one sensor.

6. The method of claim 5, wherein said additional external influence(s) is selected from the group consisting of UV, IR, magnetic field, electrostatic field, and acoustics wave (ultra sound).

7. The sensor of claim 2, wherein at least one of: (i) said at least one data processing system and/or DAQ has high impedance input; and (ii) said impedance input is greater than 10 MΩ.

8. The sensor of claim 2, wherein said at least one alternating current source has an adjustable current output.

9. The sensor of claim 2, further comprising a phase detector in communication with, and/or electrically connected to at least one of: (i) said at least one alternating current source and said at least one data processing system and/or DAQ; (ii) said at least one sensing coil and said at least one excitation coil; and (iii) said at least one sensing coil only.

10. An impedance sensing system for non-contact and non-invasive measuring and analyzing of targeted chemical and physical properties of gaseous, fluid and solid objects comprising:

(A) at least one resonance type impedance sensor of claim 1 or claim 9;
(B) at least one alternating current source with frequency sweep electrically connected to said at least one excitation coil;
(C) said at least one data processing system and/or DAQ in communication with said at least one resonance type impedance sensor or the at least one sensing coil(s), wherein the L C R parameters of said at least one sensing coil provide resonance conditions for measuring of object under test impedance at the predetermined frequency or at the predetermined frequency range; and
(D) a control system in communication with said at least one alternating current source and said at least one data processing system and/or DAQ.

11. The impedance sensing system of claim 10, further comprising a fixture to provide object under test placement in close proximity to said sensor(s), so that electromagnetic field induced by said at least one sensing coil(s) operates to penetrate into said object under test.

12. The sensing system of claim 10, further comprising a vessel for containing of said gaseous, liquid or bulk material object under test.

13. The sensing system of claim 12, wherein at least one of:
(i) said at least one sensor is configured to encompass said vessel, said at least one sensor being configured as a cylindrical multicoil inductor; and
(ii) said at least one sensor is mounted on the external or internal wall of said vessel.

14. The sensing system of claim 13, which further comprises a section of pipe, said at least one sensor(s) being installed on said section of pipe.

15. The sensing system of claim 13, further comprising at least one bypass tubing or a group of channels, said at least one sensor(s) being installed on said at least one bypass tubing or a group of channels.

16. The sensing system of claim 10, further comprising means for measuring environmental conditions outside of test object to provide reference information usable to compensate measurement error.

17. The sensing system of claim 16, wherein said means for measuring environmental conditions comprise at least one additional impedance sensor.

18. The sensing system of claim 10, wherein at least one of: (i) said at least one data processing system and/or DAQ has high impedance input; and (ii) said impedance input is greater than 10 MΩ.

19. The sensing system of claim 10, wherein said at least one alternating current source has an adjustable current output.

20. The sensor of claim 1, wherein said sensor is configured as a cylindrical multicoil inductor.

21. The sensor of claim 20, wherein said cylindrical multicoil inductor has a ferromagnetic open core.

22. The sensor of claim 21, wherein said ferromagnetic core is configured as a half pot core.

23. The sensor of claim 21, wherein said cylindrical multicoil inductor has an adjustable ferromagnetic core.

24. The sensor of claim 20, further comprising a support element, said at least two coils of said sensor configured as said multicoil inductor being mounted on said support element.

25. The sensor of claim 24, wherein said support element at least one of: (i) has low coefficient of electrical permittivity; and (ii) comprises fluorinated polymer in contact with said mounted multicoil inductor.

26. The sensor of claim 20, further comprising means for adjusting said sensor's operating frequency.

27. The sensor of claim 26, wherein said means for adjusting are at least one of: (i) an adjustable interturn step; (ii) an adjustable diameter of the at least one sensing coil(s); (iii) an adjustable number of turns in the at least one sensing coil(s); (iv) an adjustable intrinsic or distributed capacitance of the at least one sensing coil(s); and (v) a changeable basket winding that operates to decrease or increase self capacitance of the at least one sensing coil(s).

28. The sensor of claim 1, further comprising a support element, wherein said at least two coils are mounted on said support element.

29. The sensor of claim 28, wherein at least one of: (i) said multicoil inductor is planar; and (ii) said support element is a printed circuit board ("PCB") type or flexible support element.

30. The sensor of claim 1, wherein said at least one sensing coil and said at least one excitation coil are spatially separated from one another.

31. The sensor of claim 1, wherein said object under test is at least one of: conductive, semi-conductive, and non-conductive.

32. The sensor of claim 1, wherein said at least one excitation coil and said at least one sensing coil are separate windings and are electromagnetically coupled.

33. The sensor of claim 1, wherein said at least one excitation coil and said at least one sensing coil are in a single winding and are electromagnetically coupled.

34. The sensor of claim 33, wherein said at least one excitation coil and said at least one sensing coil are arranged in series and are electromagnetically coupled.

35. The sensor of claim 33, wherein said at least one excitation coil and said at least one sensing coil share one or more turns of said single winding and are electromagnetically coupled.

36. A method of measuring chemical and physical properties of an object by at least one resonance type impedance sensor of claim 9, said method comprising:
(A) measuring, in the absence of an object under test at fixed frequency which is near resonance frequency of said sensing coil of said at least one sensor, at least one of:
(i) an amplitude of said sensing coil of said at least one sensor and phase shift between voltage and current of said sensing coil, and
(ii) phase shift of said sensing coil relative to said excitation coil of said at least one sensor;
(B) placing the object under test comprising at least one analyte in close proximity of said at least one sensor, in order to provide penetration of the electromagnetic field induced by said at least one sensor into said object under test;
(C) measuring, in the presence of said object at fixed frequency which is near resonance frequency of said sensing coil of said at least one sensor, at least one of:
(ii) an amplitude of said sensing coil of said at least one sensor and phase shift between voltage and current of said sensing coil, and
(ii) phase shift of said sensing coil relative to said excitation coil of said at least one sensor;
(D) calculating changes in said amplitude and said phase shift induced by electromagnetic interaction between said at least one sensor and said object to determine impedance of said object under test; and (E) matching said impedance with predetermined calibration data to determine said chemical or physical properties of said object under test.

37. The method of claim 36, further comprising applying additional external influence(s) on said object under test to improve sensitivity of said at least one sensor.

38. The method of claim 37, wherein said additional external influence(s) is selected from the group consisting of UV, IR, magnetic field, electrostatic field, and acoustics wave (ultra sound).

39. A method of measuring chemical and physical properties of an object by at least one sensing system of claim 10, said method comprising:
  (A) measuring a resonant frequency (self-resonance frequency) and amplitude of said sensor(s) in the absence of an object under test;
  (B) placing an object under test comprising at least one analyte in close proximity of said sensor(s) in order to provide penetration of said electromagnetic field induced by said sensor(s) into said object under test;
  (C) measuring a resonant frequency and amplitude of sensor(s) in the presence of said object;
  (D) calculating changes in amplitude and resonant frequency induced by electromagnetic interaction between said sensor(s) and said object to determine impedance of said object under test; and
  (E) matching said impedance with predetermined calibration data to determine said chemical or physical properties of said object under test.

40. The method of claim 39, further comprising monitoring of time-related changes in impedance and correlating said chemical or physical properties of said object under test to said time-related changes in impedance.

41. The method of claim 39, further comprising applying additional external influence(s) on said object under test to improve sensitivity of said sensing system.

42. The method of claim 41, wherein said additional external influence(s) is selected from the group consisting of UV, IR, magnetic field, electrostatic field, and acoustics wave (ultra sound).

43. A method of measuring chemical and physical properties of an object by at least one sensing system of claim 10, said method comprising:
  (A) measuring, in the absence of an object under test at fixed frequency which is near resonance frequency of said sensing coil of said at least one sensor, at least one of:
    (i) an amplitude of said sensing coil of said at least one sensor and phase shift between voltage and current of said sensing coil, and
    (ii) phase shift of said sensing coil relative to said excitation coil of said at least one sensor;
  (B) placing the object under test comprising at least one analyte in close proximity of said at least one sensor, in order to provide penetration of electromagnetic field induced by said at least one sensor into said object under test;
  (C) measuring, in the presence of said object at fixed frequency which is near resonance frequency of said sensing coil of said at least one sensor, at least one of:
    (ii) an amplitude of said sensing coil of said at least one sensor and phase shift between voltage and current of said sensing coil, and
    (ii) phase shift of said sensing coil relative to said excitation coil of said at least one sensor;
  (D) calculating changes in said amplitude and said phase shift induced by electromagnetic interaction between said sensor and object to determine impedance of said object under test; and
  (E) matching said impedance with predetermined calibration data to determine said chemical or physical properties of said object under test.

44. The method of claim 43, further comprising applying additional external influence(s) on said object under test to improve sensitivity of said sensing system.

45. The method of claim 44, wherein said additional external influence(s) is selected from the group consisting of UV, IR, magnetic field, electrostatic field, and acoustics wave (ultra sound).

\* \* \* \* \*